United States Patent
Sperling et al.

(10) Patent No.: US 8,167,798 B2
(45) Date of Patent: May 1, 2012

(54) METHODS AND APPARATUS FOR PERFORMING MINIMALLY INVASIVE SURGERY

(75) Inventors: Jason Scott Sperling, Upper Saddle River, NJ (US); Jeffrey A. Kinsberg, Matawan, NJ (US); Cristy J. Richards, Matawan, NJ (US)

(73) Assignee: Jason Scott Sperling, Upper Saddle River, NJ (US)

( * ) Notice: Subject to any disclaimer, the term of this patent is extended or adjusted under 35 U.S.C. 154(b) by 161 days.

(21) Appl. No.: 12/692,139

(22) Filed: Jan. 22, 2010

(65) Prior Publication Data

US 2010/0185059 A1 Jul. 22, 2010

Related U.S. Application Data

(63) Continuation-in-part of application No. 11/370,250, filed on Mar. 7, 2006, now Pat. No. 7,651,465.

(60) Provisional application No. 60/659,303, filed on Mar. 7, 2005.

(51) Int. Cl.
*A61B 1/32* (2006.01)
(52) U.S. Cl. ........................................ 600/219; 600/222
(58) Field of Classification Search .......... 600/184–200, 600/201–246
See application file for complete search history.

(56) References Cited

U.S. PATENT DOCUMENTS

| 810,675 | A | | 1/1906 | Richter |
|---|---|---|---|---|
| 4,300,541 | A | | 11/1981 | Burgin |
| 4,747,394 | A | * | 5/1988 | Watanabe ..................... 600/232 |
| 4,971,037 | A | | 11/1990 | Pelta |
| 4,989,587 | A | | 2/1991 | Farley |
| 5,067,477 | A | | 11/1991 | Santangelo |
| 5,088,472 | A | | 2/1992 | Fakhrai |
| RE34,150 | E | | 12/1992 | Santilli et al. |
| 5,569,300 | A | * | 10/1996 | Redmon ....................... 606/207 |
| 5,616,117 | A | * | 4/1997 | Dinkler et al. ................ 600/232 |
| 5,882,299 | A | | 3/1999 | Rastegar et al. |
| 5,967,972 | A | | 10/1999 | Santilli et al. |
| 5,984,867 | A | | 11/1999 | Deckman et al. |
| 6,099,468 | A | | 8/2000 | Santilli et al. |
| 6,224,545 | B1 | | 5/2001 | Cocchia et al. |
| 6,309,349 | B1 | | 10/2001 | Bertolero et al. |
| 6,322,500 | B1 | | 11/2001 | Sikora et al. |
| 6,821,247 | B2 | | 11/2004 | Vierra et al. |
| 7,651,465 | B1 | | 1/2010 | Sperling et al. |

(Continued)

FOREIGN PATENT DOCUMENTS

WO 98/27869 A1 7/1998

*Primary Examiner* — Eduardo C Robert
*Assistant Examiner* — Christina Negrelli
(74) *Attorney, Agent, or Firm* — Lando & Anastasi, LLP

(57) ABSTRACT

A device for expanding an elongate opening formed in a skin layer of a patient includes a first arm for engaging one side of the opening and a second arm for engaging the other side of the opening. The device further includes a spreader mechanism, coupled to at least one of the first and second arms, to move the at least one of the first and second arms to widen the opening. The at least one arm is configured to move between a retracted position in which the at least one arm is positioned next to the other arm and an extended position in which the at least one arm is extended to expand the opening. Other embodiments of the device as well as methods for performing a medical procedure are further disclosed.

18 Claims, 34 Drawing Sheets

U.S. PATENT DOCUMENTS

| | | |
|---|---|---|
| 2001/0018556 A1 | 8/2001 | Paolitto et al. |
| 2001/0041828 A1 | 11/2001 | Deckman et al. |
| 2002/0049369 A1 | 4/2002 | Spence et al. |
| 2002/0099269 A1 | 7/2002 | Martin et al. |
| 2002/0099272 A1 | 7/2002 | Looney et al. |
| 2004/0242968 A1 | 12/2004 | Hill et al. |

* cited by examiner

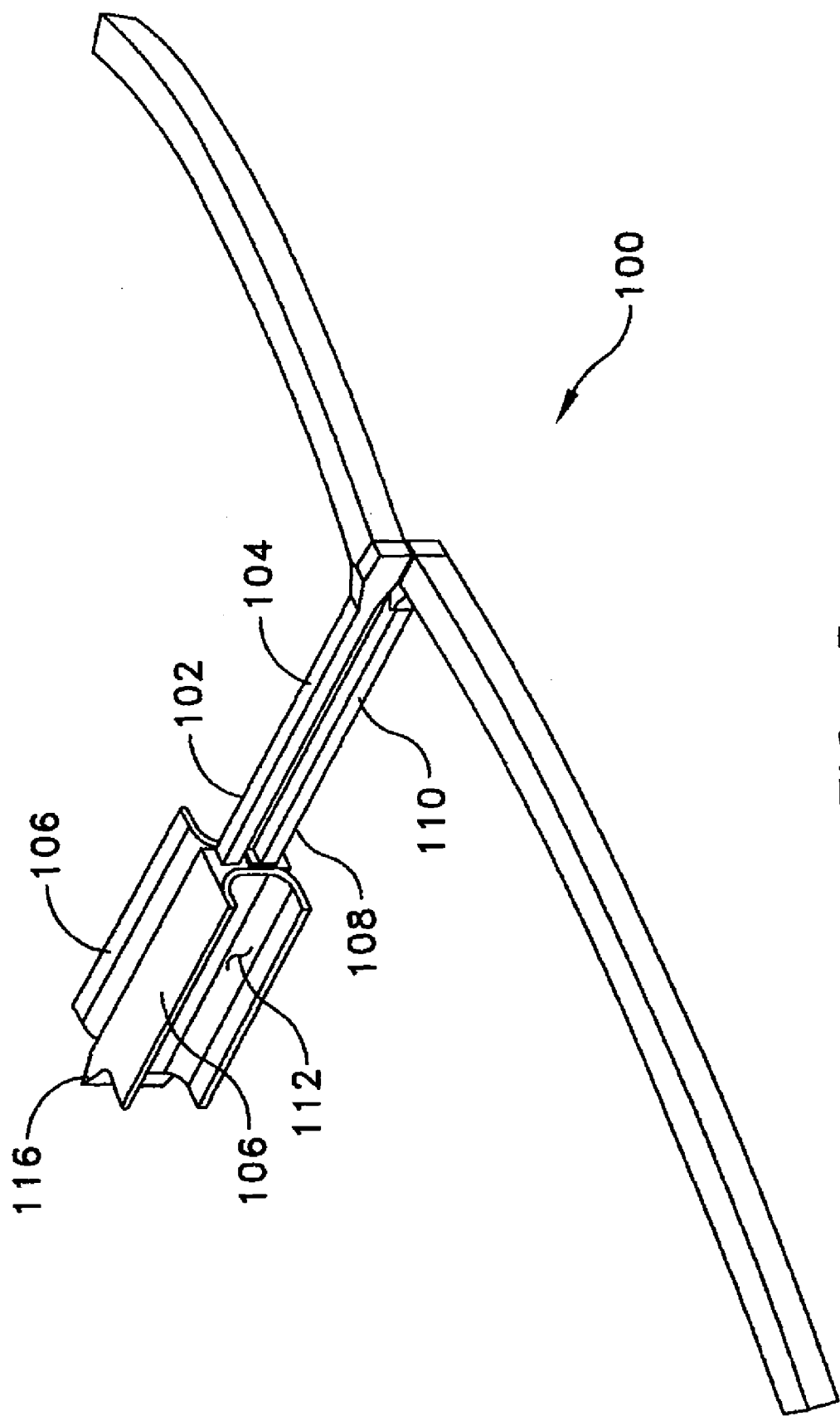

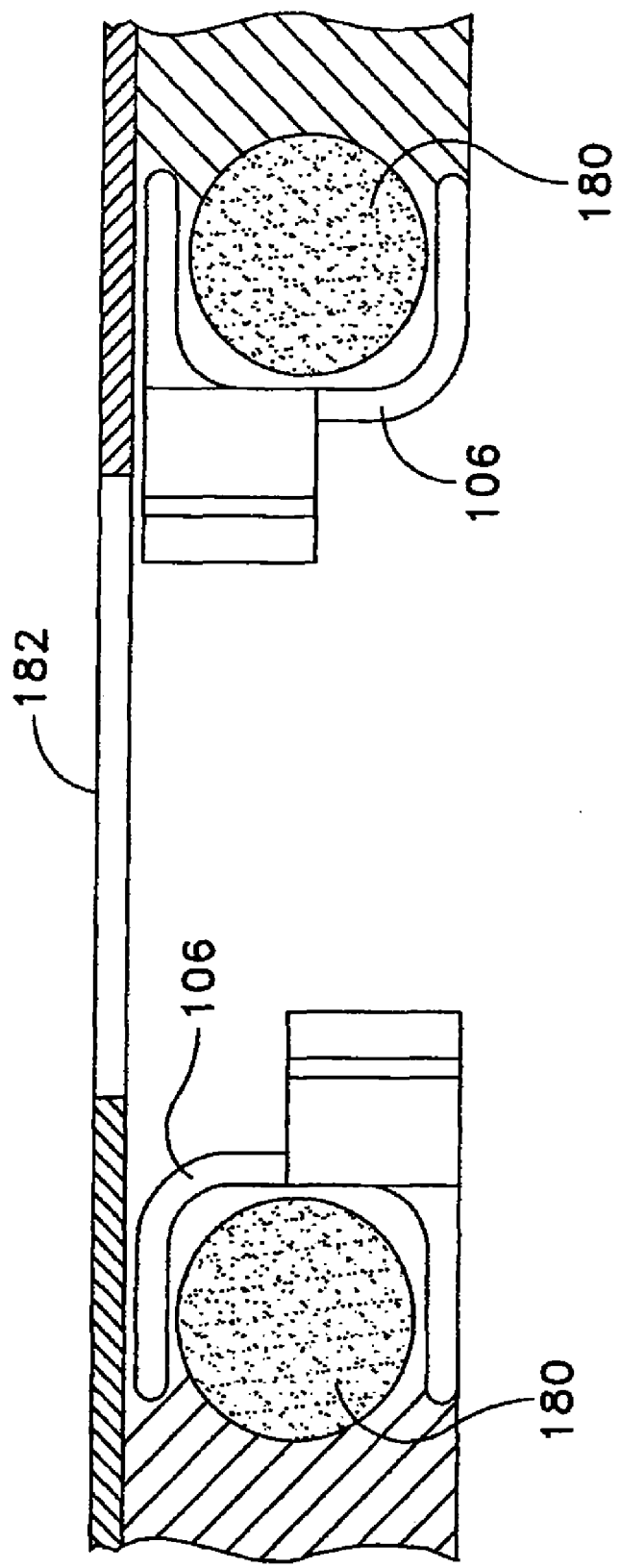

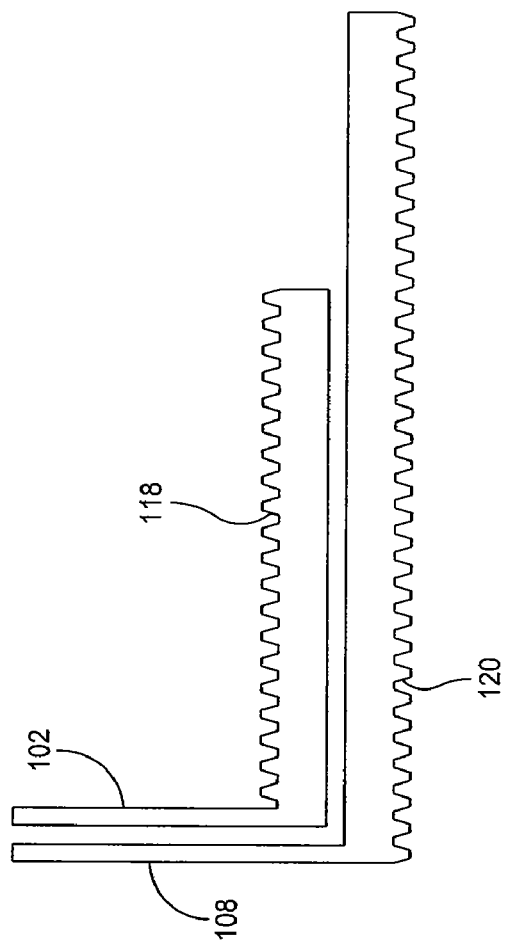
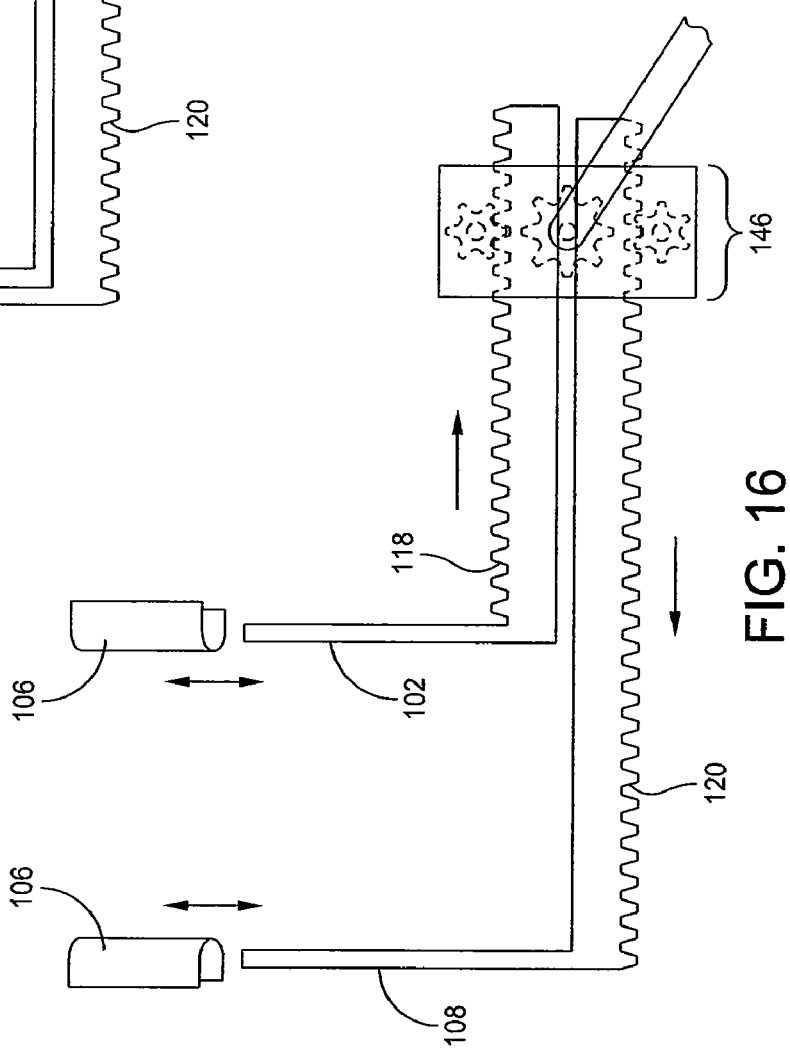

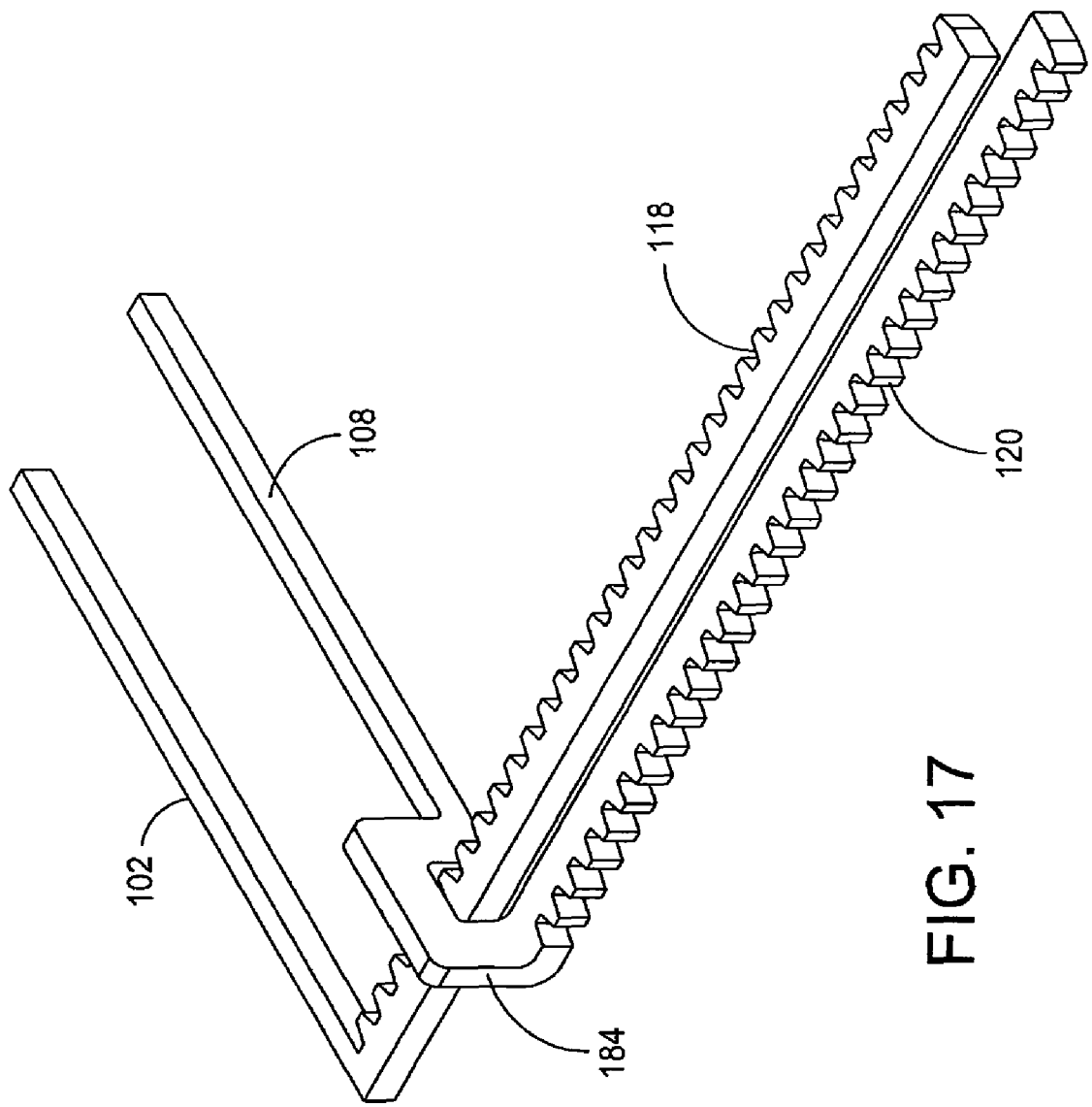

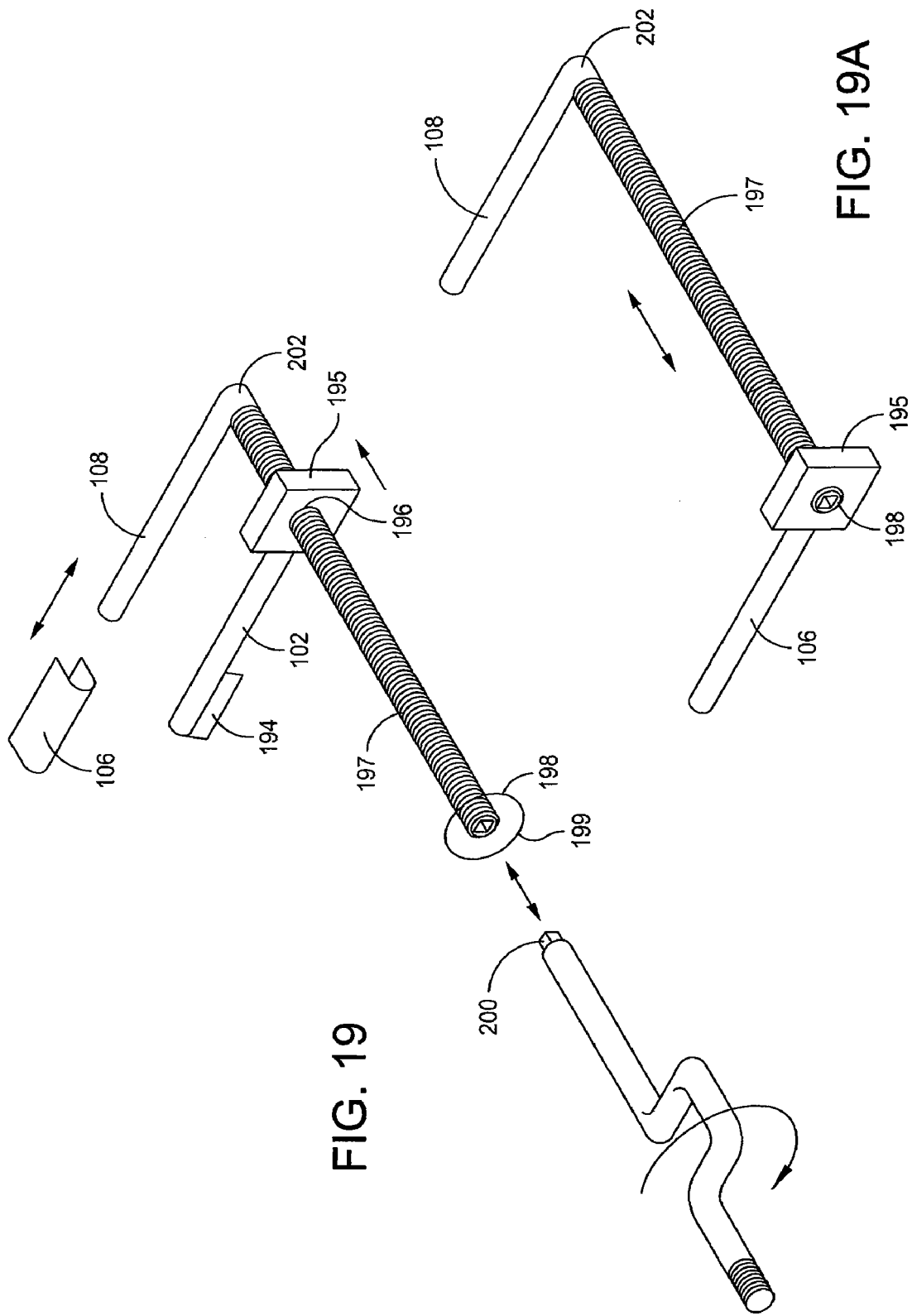

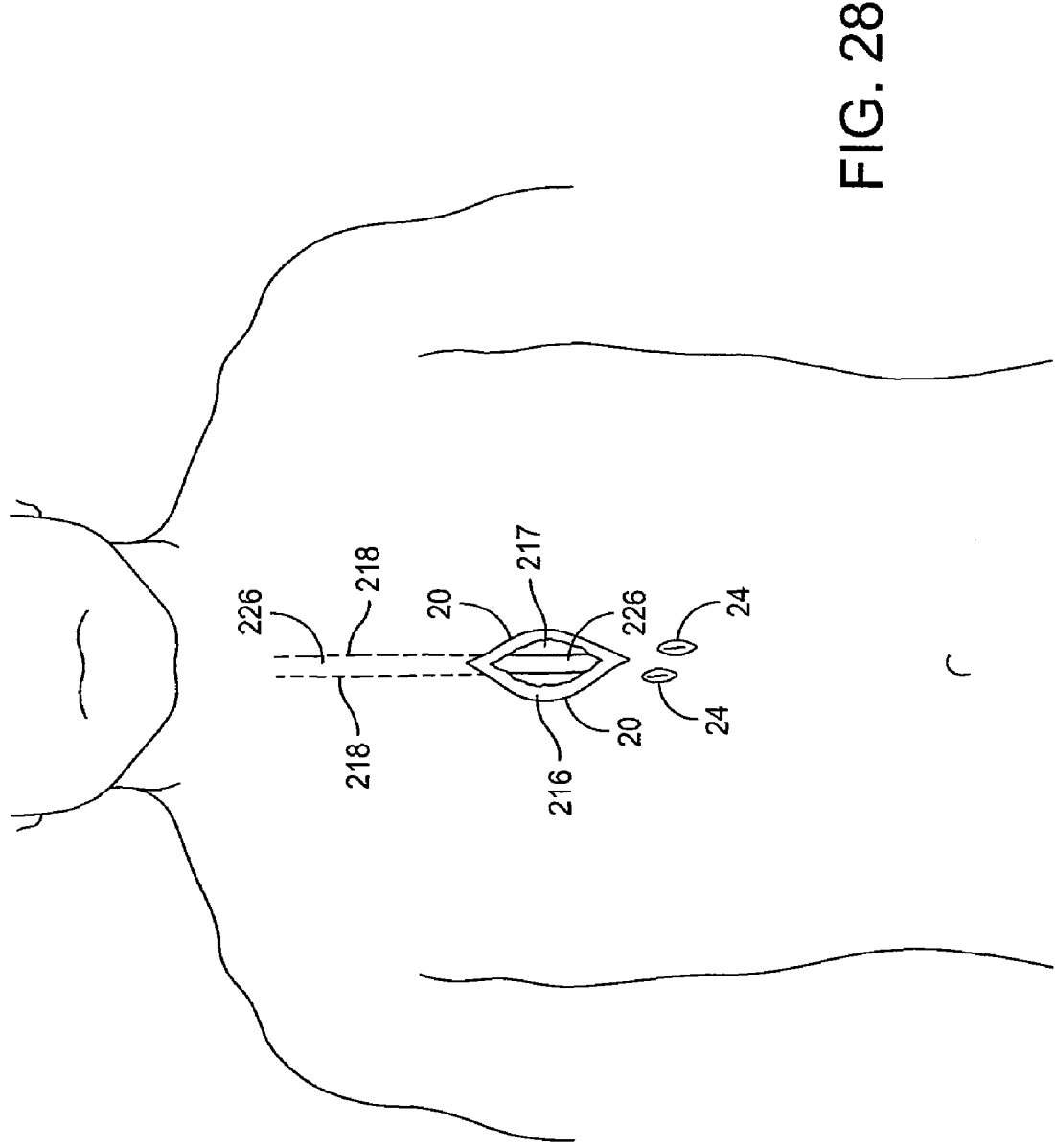

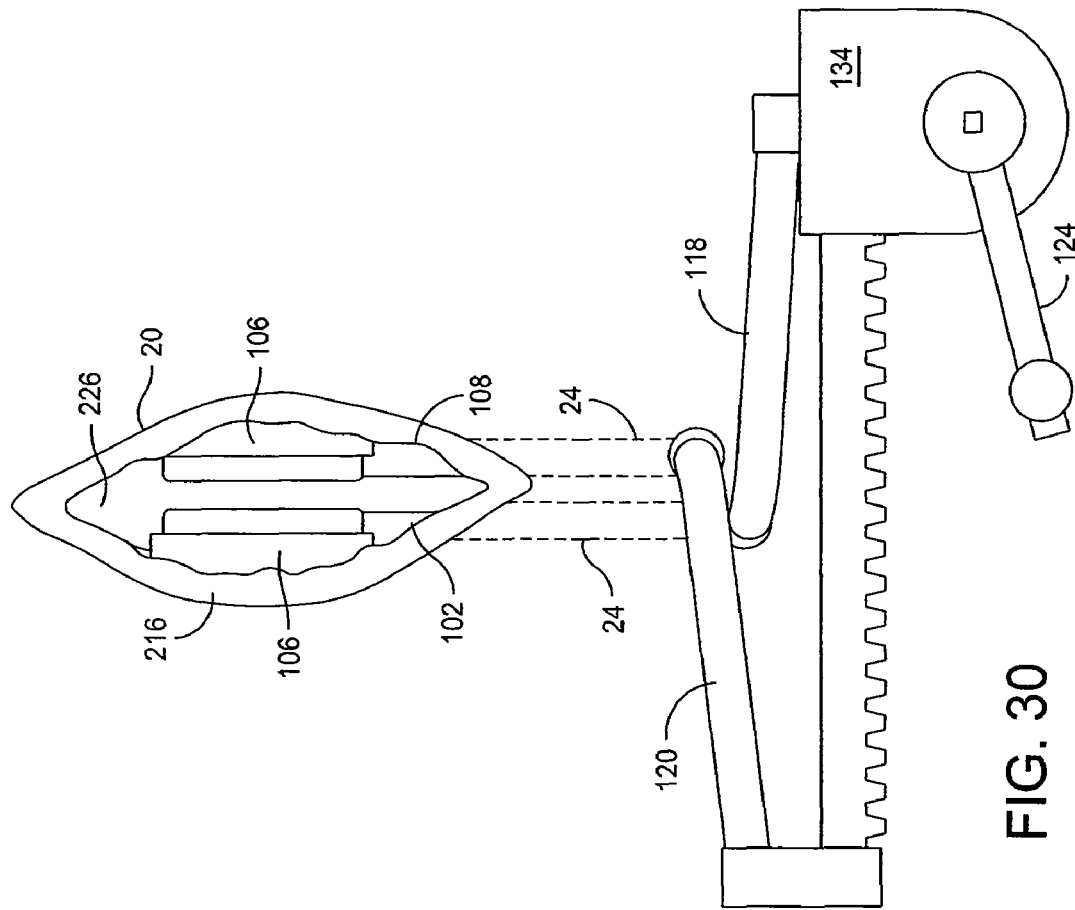
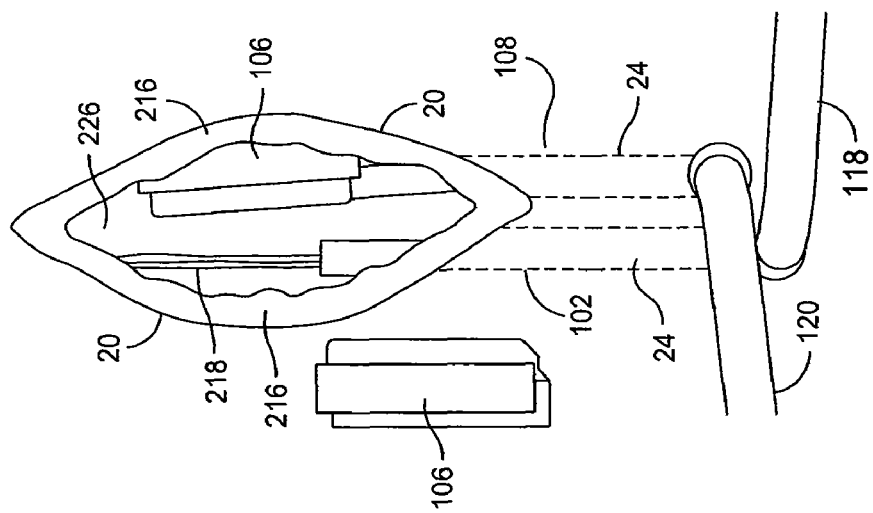
FIG. 30
FIG. 30A

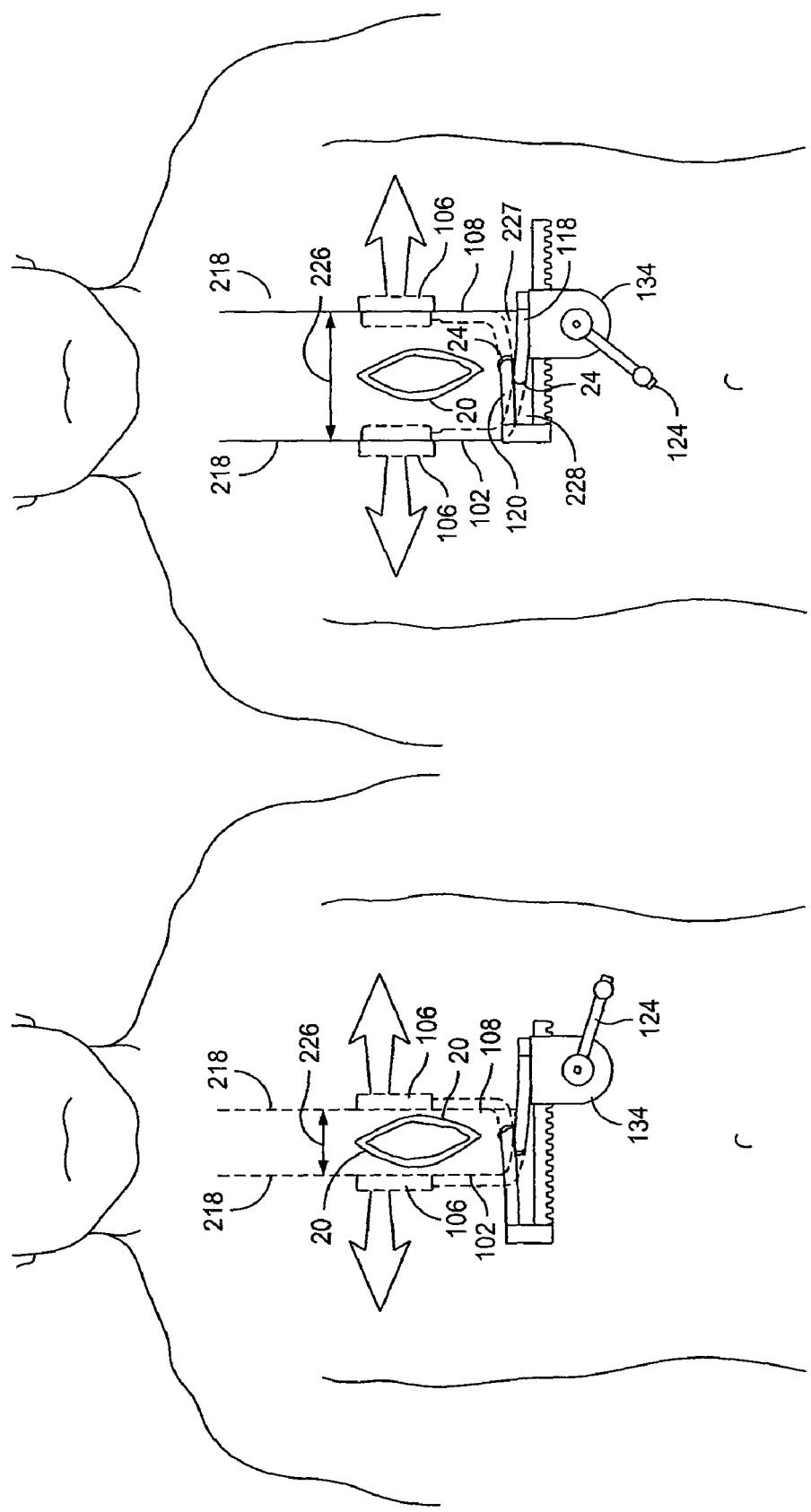

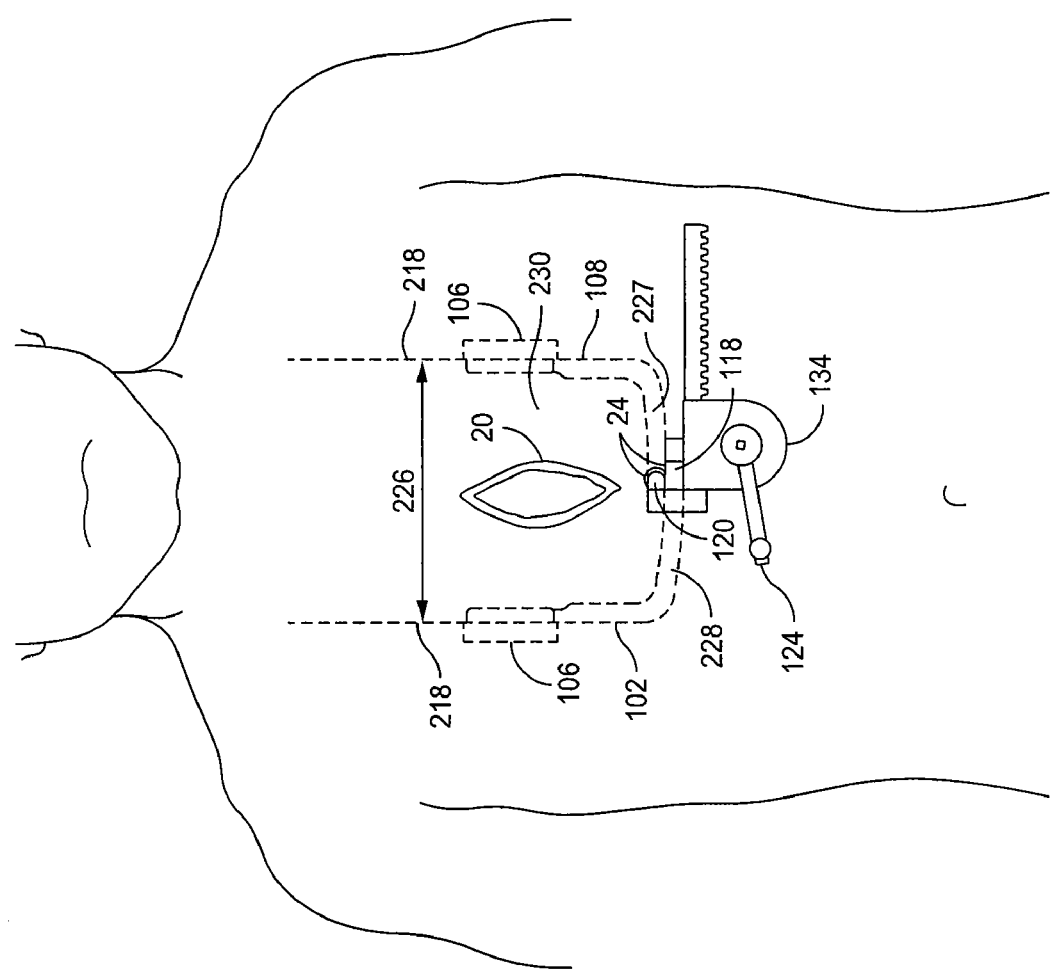

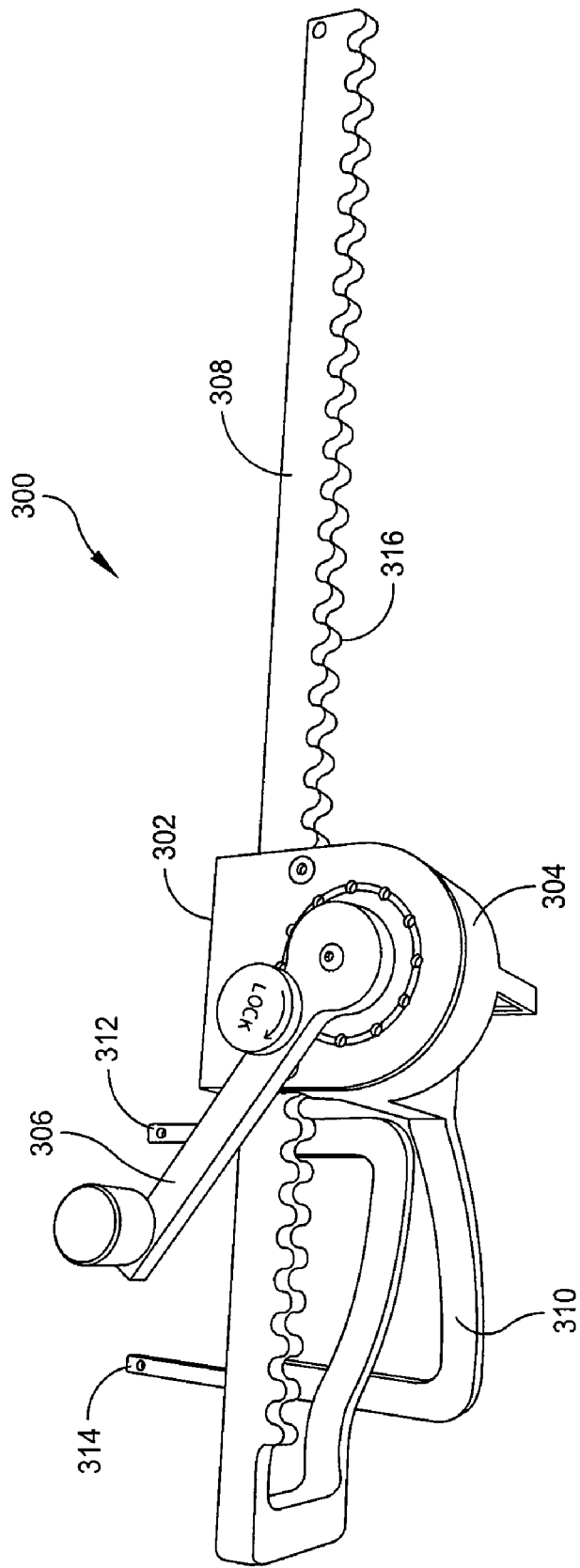

METHODS AND APPARATUS FOR PERFORMING MINIMALLY INVASIVE SURGERY

RELATED APPLICATIONS

This application is a continuation-in-part of U.S. patent application Ser. No. 11/370,250, entitled "METHODS AND APPARATUS FOR PERFORMING MINIMALLY INVASIVE SURGERY, filed on Mar. 7, 2006, which claimed priority to U.S. Provisional Application Ser. No. 60/659,303, entitled "METHODS AND APPARATUS FOR PERFORMING MINIMALLY INVASIVE SURGERY," filed on Mar. 7, 2005, both of which are herein incorporated by reference in their entirety.

BACKGROUND OF THE DISCLOSURE

1. Field of the Disclosure

This disclosure relates generally to methods and devices for performing surgery, and more particularly, to methods and devices for performing minimally invasive surgery, such as cardiac surgery, including, but not limited to, coronary artery bypass grafting, valvular, dysrhythmia and aortic surgery, as well as thoracic surgical procedures.

2. Discussion of Related Art

Coronary artery disease is the largest or one of the largest causes of death in the United States. Interventions for coronary artery disease include education, medication, percutaneous coronary intervention, such as balloon angioplasty and stenting, and coronary bypass surgery.

Coronary artery bypass surgery is the most common type of heart surgery, with over 300,000 people having successful surgery in the United States each year. As is well known, arteries can become clogged over time by the build-up of fatty plaque in the artery wall. Coronary bypass surgery bypasses the diseased artery with a new blood vessel taken from the leg (greater saphenous vein) or an artery from the chest or arm. This procedure creates a new route for blood to flow.

Coronary artery bypass surgery is typically performed through an open chest exposure (i.e., to access and circumvent obstructed coronary arteries). A common approach involves making a 15-20 cm long incision in the skin overlying the breastbone, and splitting and separating the sternum to provide full access to the heart. With reference to FIG. 1, during coronary artery bypass surgery, the patient's breastbone 10 (sternum) is divided by means of a sternal saw. As stated above, a typical incision 12 is approximately 15-20 cm long. After appropriate bypass conduits are taken (e.g., a vein from the patient's leg), a sternal retractor is placed to spread the skin and breastbone to expose the heart and vessels for the bypass procedure. During the procedure, the heart may be stopped, and the patient's blood is sent through a heart-lung machine. This procedure typically takes three to five hours to perform, depending on the number of bypasses required. Three to four smaller incisions may be made inferior to the initial incision for drain placement around the heart after the procedure is completed. At the end of the procedure, the patient's breastbone is wired back together and the muscle and skin are closed as well with absorbable sutures.

The long incision 12 described above, which starts from the very top of the breastbone and extends the bottom of the breastbone, cuts not only the breastbone, but tissue and muscle as well. During the operation, a sternal retractor is situated above the cavity to spread the skin, tissue, muscle and breastbone. This large incision may cause several potential negative side effects. Of all the layers of body tissue, the skin is the most innervated with sensory nerves, as compared to muscle and breastbone. Further, closure of the pectoral muscles must be done in a fashion that results in much more tension on the muscles than the native state. This may result in extreme pain at rest which is exacerbated by any action that stretches the skin or muscle, which can lead to respiratory complications and general inactivity due to splinting. There may also be associated negative psychological effects.

Experience from other surgical procedures has shown that minimized surgical incisions result in shorter intensive care unit and hospital stays, less complications, less pain, and an overall better experience for the patient. For example, prior techniques in gallbladder removal (cholecystectomy) involved a substantial incision of 12-15 cm in the abdomen, which results in expected increased patient discomfort. When laparoscopic cholecystectomy was developed, which involves making four small incisions (each between 0.5 and 1.2 cm long) and the use of video equipment, the results was shorter hospital stays, less complications and quicker patient recovery.

Percutaneous coronary intervention ("PCI") was developed as a less invasive way than coronary artery bypass grafting to treat coronary artery disease. PCI has progressed from balloon angioplasty, to stents, to drug eluting stents. However, PCI may not be suitable for patients who are diabetic or who have three or more artery blockages, according to the official recommendations of the American College of Cardiology.

Although there are examples of "minimal" invasive coronary artery bypass surgery, such surgery typically involves bypassing only left sided, anterior coronary vessels, through a limited rib spreading incision. This operation is only used for patients whose entire set of blockages can be bypassed through this smaller incision which represents a minority of patients.

Minimally invasive approaches to all types of operations are desirable because of the advantages of less scarring and pain, shorter hospital stays and recovery time. With minimally invasive approaches, such approaches generally try to avoid splitting the sternum and may use a series of incisions to gain adequate visualization and access the patient's heart. Rarely, with these approaches, is it possible to use videoscopic imaging systems or robotic guidance devices. While these techniques may provide advantages when dealing with a limited set of anatomic heart problems, they are not widely adopted due to their cumbersome nature, and the limited mobility through relatively fixed bony and muscular structures. There is concern that sub-par results may be obtained. In addition with small incisions, reduced three-dimensional visibility and perceptual orientation may increase some risk to the patient.

SUMMARY OF THE DISCLOSURE

One aspect of the disclosure is directed to a method of performing coronary artery bypass and other open heart procedures. The method comprises: making at least one small incision of approximately 5 cm above the breastbone of the patient, with or without mobilizing the sternal envelope (fascia) in order to spare division of the pectoral muscles; dividing the entire breastbone to create an opening; inserting a device within the opening below the skin (and possibly, muscle) layer; expanding the device to increase the opening; performing a medical procedure; retracting the device; and closing the opening.

Another aspect of the disclosure is directed to a device for expanding an opening within a patient having a length of 5 cm or less. The device comprises a central body, and at least one arm coupled to the body. The arm is adapted to move between a retracted position in which the arm is housed within the central body and an extended position in which the arm is extended to expand the opening.

Yet another aspect of the disclosure is directed to a method of performing a medical procedure. The method comprises: making an incision in a patient; inserting a device through the incision and below a skin layer; expanding the device to expand an opening below the skin layer; and performing the medical procedure. In one embodiment, the opening is a division in the breastbone of a patient. The medical procedure may include pectoralis-sparing open heart surgery.

A further aspect of the disclosure is directed to a device for expanding an elongate opening formed in a skin layer of a patient, with the opening having opposite sides. The device comprises a first arm for engaging one side of the opening, a second arm for engaging the other side of the opening, and a spreader mechanism, coupled to at least one of the first and second arms, to move the at least one of the first and second arms to widen the opening. The at least one arm is adapted to move between a retracted position in which the at least one arm is positioned next to the other arm and an extended position in which the at least one arm is extended to expand the opening.

Embodiments of the device may further include the first and second arms comprising a distracter shaft and a support channel releasably secured to the distracter shaft. The support channel may be configured to engage a side of the opening. The support channel may further include a C-shaped surface adapted engage body tissue below the skin layer to widen the opening. The support channel may have a length of less than 5 cm. The support channel may have a wedge-shaped leading edge. In one embodiment, one of the first and second arms comprises an actuator member coupled to the spreader mechanism. The spreader mechanism comprises a gear box and a device for turning the gear box. The gear box comprises a first gear segment secured to the actuator member of the first arm and a gear wheel to engage the first and second gear segments. The gear box may further comprise a second gear segment secured to the actuator member of the second arm. A mount may be formed on the spreader mechanism, the mount being configured to secure the device to a support assembly. In another assembly, the spreader mechanism may comprise a scissor mechanism.

Another aspect of the disclosure is directed to a method of performing an open heart surgery procedure. The method comprises: making at least one small incision of approximately 5 cm above a breastbone of the patient; dividing the breastbone to create an opening; inserting a device within the opening below a skin layer; expanding the device to increase the opening; performing a medical procedure; retracting the device; and closing the opening. In one embodiment, the step of expanding the device includes moving at least one arm of the device to widen the opening.

Another aspect of the disclosure is directed to a device for expanding an elongate opening formed in a skin layer of a patient, with the opening having opposite sides. The device comprises a first arm for engaging one side of the opening and a second arm for engaging the other side of the opening. The first and second arms are configured to engage the sides of the opening below the skin layer. The device further comprises means for moving at least one of the first and second arms for widening the opening. The at least one arm is adapted to move between a retracted position in which the at least one arm is positioned next to the other arm and an extended position in which the at least one arm is extended to expand the opening.

In one embodiment, the means for moving at least one of the first and second arms comprises a spreading mechanism disposed above the skin layer and coupled to the at least one of the first and second arms.

An additional aspect of the disclosure is directed to a method of performing a medical procedure. The method comprises: making an incision in a patient; inserting a device below the skin layer of the patient; expanding the device to expand an opening below the skin layer; and performing the medical procedure. In one embodiment, the opening is a division in the breastbone of a patient. In another embodiment the medical procedure is pectoralis-sparing open heart surgery.

Another aspect of the disclosure is directed to a device for expanding an opening formed below a skin layer of a patient, with the opening having opposite sides. In one embodiment, the device includes a first L-shaped member having a first arm and a first actuator connected to the first arm. The first arm of the first L-shaped member is configured to engage one side of the opening. The device further includes a second L-shaped member having a second arm and a second actuator connected to the second arm. The second arm of the second L-shaped member is configured to engage the other side of the opening. The first L-shaped member is configured to nest within the second L-shaped member with both members maintaining a generally identical orientation. The device further includes a spreader mechanism, coupled to at least one of the first and second actuator members, to move the first and second arms apart from one another. The first and second arms are configured to move between a retracted position in which the first and second arms are positioned next to one another and an extended position in which the first and second arms are extended to expand the opening.

Embodiments of the device may include configuring each of the first and second arms with a distracter shaft and a support channel releasably secured to the distracter shaft. The support channel is configured to engage a side of the opening. The support channel may include a C-shaped surface adapted to engage body tissue below the skin layer to widen the opening. The arrangement is such that arms of the device may be inserted through at least one site that is separate from a skin incision. The device may be configured to spread apart the opening without directly spreading apart edges of the skin layer. In one embodiment, at least one arm or support channel includes an illumination element configured to direct light below the device when viewed from above. The spreader mechanism may include a gear box and a device for turning the gear box.

A further aspect of the disclosure is directed to a device for expanding an opening formed below a skin layer of a patient, with the opening having opposite sides. In one embodiment, the device includes a first arm for engaging one side of the opening, a second arm for engaging the other side of the opening, a first actuator member connected to the first arm, and a second actuator member connected to the second arm. The first arm includes a segment that overlays the second actuator member. The device further includes a spreader mechanism, coupled to at least one of the first and second actuator members, to move the arms apart horizontally. The arms are adapted to move between a retracted position in which the arms are positioned next to one another and an extended position in which the arms are extended to expand the opening.

Another aspect of the disclosure is directed to a device for expanding an opening formed below a skin layer of a patient, with the opening having opposite sides. In one embodiment, the device includes a first arm for engaging one side of the opening, a second arm for engaging the other side of the opening, a first actuator member attached to or reversibly attachable to the first arm, a second actuator member attached to or reversibly attachable to the second arm, a first spreader mechanism configured to be attached to an operating table and coupled to the first actuator member, and a second spreader mechanism configured to be attached to an operating table and coupled to the second actuator member. The first and second spreader mechanisms are configured to move the first and second arms apart. The first and second arms are adapted to move between a retracted position in which the arms are positioned next to one another and an extended position in which the arms are extended to expand the opening.

Embodiments of the device may include providing the first and second spreader mechanisms with a cable and pulley system to move the first and second actuator members. The first and second spreader mechanisms may include a rack and pinion assembly to move the first and second actuator members.

Yet another aspect of the disclosure is directed to a device for expanding an opening formed below a skin layer of a patient, with the opening having opposite sides. In one embodiment, the device includes a first arm for engaging one side of the opening and a second arm for engaging the other side of the opening. The first arm is attached to a base and the second arm is attached to an actuator that traverses through the base. The device further includes a crankshaft attached to or reversibly coupled to one of the actuator and the base and a spreader mechanism, actuated by the crankshaft, to move the first and second arms apart. The arms are adapted to move between a retracted position in which the arms are positioned next to one another and an extended position in which the arms are extended to expand the opening.

Another aspect of the disclosure is directed to a method for performing surgery on organs located below a skin and muscle layer through a small skin incision. The method comprises: making a small access incision in the skin; surgically separating a tissue plane between a normally adherent and adjacently layered muscle and fatty tissue radiating outward from the skin; utilizing a device to spread divided deeper tissues apart below the level of the skin without directly contacting the skin edges of the access incision; and performing a surgical procedure. In one embodiment, the small access incision is generally less than 8 cm long. The device may be configured with a crankshaft driver that traverses from external to, to internal to, the skin in order to actuate and spread the device apart below the intact skin adjacent to the access incision.

A further aspect of the disclosure is directed to a method for performing heart surgery through a small skin incision comprising: making a small access incision in the skin overlying the breastbone; surgically separating a tissue plane between the normally adherent and adjacently layered pectoralis muscle and fatty tissue radiating outward from the skin incision underneath adjacent areas of intact skin; dividing the pectoralis muscles and the breastbone vertically in the midline; utilizing a device to spread apart the breastbone below the level of the skin without directly contacting the skin edges of the access incision; and performing heart surgery. In one embodiment, the small access incision is generally less than 8 cm long. The device may be configured with a crankshaft driver that traverses from external to, to internal to, the skin in order to actuate and spread the device apart below the intact skin adjacent to the access incision.

Yet another aspect of the disclosure is directed to a method for instructing a surgeon to perform heart surgery through a small skin incision comprising: directing the surgeon to create a small access incision in the skin overlying the breastbone; surgically separating the tissue plane between the normally adherent and adjacently layered pectoralis muscle and fatty tissue radiating outward from the skin incision underneath adjacent areas of intact skin; dividing the pectoralis muscles and the breastbone vertically in the midline; utilizing a device to spread apart the breastbone below the level of the skin without directly contacting the skin edges of the access incision; and performing heart surgery. In one embodiment, the surgeon is further instructed to actuate the device by utilizing a crankshaft driver that traverses from external to, to internal to, the skin.

One additional aspect of the disclosure is directed to a method for instructing a surgeon to perform surgery through a small skin incision comprising: directing the surgeon to create a small access incision in the skin overlying the region of interest; surgically separating the tissue plane between the normally adherent and adjacently layered muscle and fatty tissue radiating outward from the skin incision underneath adjacent areas of intact skin; dividing the muscle layer; and utilizing a device to spread apart the deeper tissues below the level of the skin without directly contacting the skin edges of the access incision, and performing a surgical procedure. In one embodiment, the surgeon is further instructed to actuate the device by utilizing a crankshaft driver that traverses from external to, to internal to, the skin.

The present disclosure will be more fully understood after a review of the following drawing figures, detailed description and claims.

DESCRIPTION OF THE DRAWINGS

For a better understanding of the present disclosure, reference is made to the drawing figures which are incorporated herein by reference and in which:

FIG. 5 is a perspective view of a device of another embodiment of the disclosure for performing a method of coronary artery surgery, with arms of the device being shown in a retracted position;

FIG. 15 is a cross-sectional view of a patient's breastbone being divided by a device of embodiments of the present disclosure;

FIGS. 16 and 16A are side elevational views of components of a device of another embodiment of the disclosure;

FIG. 17 is a perspective view of an arm of a device of another embodiment of the disclosure with a segment of the arm overlaying an actuator;

FIGS. 19 and 19A are exploded perspective views of an embodiment of a device having a crankshaft that is used to operate a nut-and-bolt mechanism to spread arms of the device apart;

FIGS. 21 and 21A are another embodiment of a device having a crankshaft that is used to turn gears that interact with an actuator in a rack-and-pinion mechanism to spread arms of the device apart;

FIG. 28 illustrates a completely divided breastbone underneath the largely intact skin and fatty tissue block;

FIGS. 30 and 30A are enlarged views showing reversibly attachable support channels of a device being joined to the arms of the device via the small access incision;

FIGS. 31 and 31A illustrate stages of a device being deployed, and the arms of the device gradually extending apart the divided breastbone edges;

FIG. 32 illustrates a device in a fully deployed state, spreading apart the breastbone extensively underneath the largely intact skin and fatty tissue;

FIG. 34 illustrates a device of another embodiment of the disclosure.

DETAILED DESCRIPTION OF THE DISCLOSURE

Figure 1:
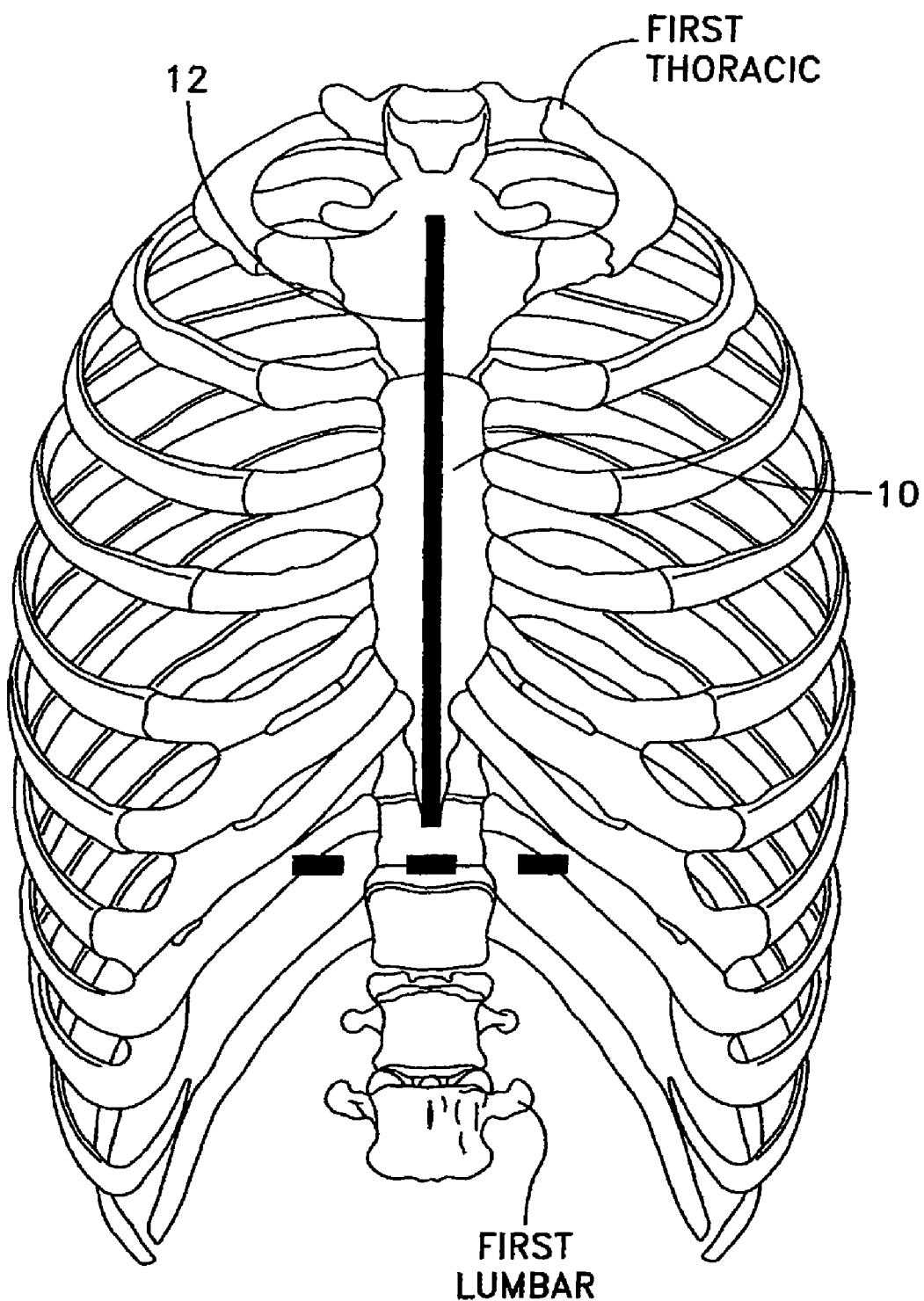
FIG. 1 is a representation of incisions made on a patient pursuant to a prior method of performing coronary artery surgery.

This disclosure is not limited in its application to the details of construction and the arrangement of components set forth in the following description or illustrated in the drawings. The disclosure is capable of other embodiments and of being practiced or of being carried out in various ways. Also, the phraseology and terminology used herein is for the purpose of description and should not be regarded as limiting. The use of "including," "comprising," or "having," "containing," "involving," and variations thereof herein, is meant to encompass the items listed thereafter and equivalents thereof as well as additional items.

Generally, coronary artery bypass grafting procedures are performed one of two ways —beating heart surgery and non-beating heart surgery. The non-beating heart procedure uses a heart-lung cardiopulmonary bypass machine, in which the heart is purposely arrested (stopped) and the patient's blood is recycled and oxygenated by the machine. Beating heart surgery (also known as "off-pump" coronary bypass surgery) was performed before non-beating heart surgery and has recently been rejuvenated as a modern technique.

Figure 2:
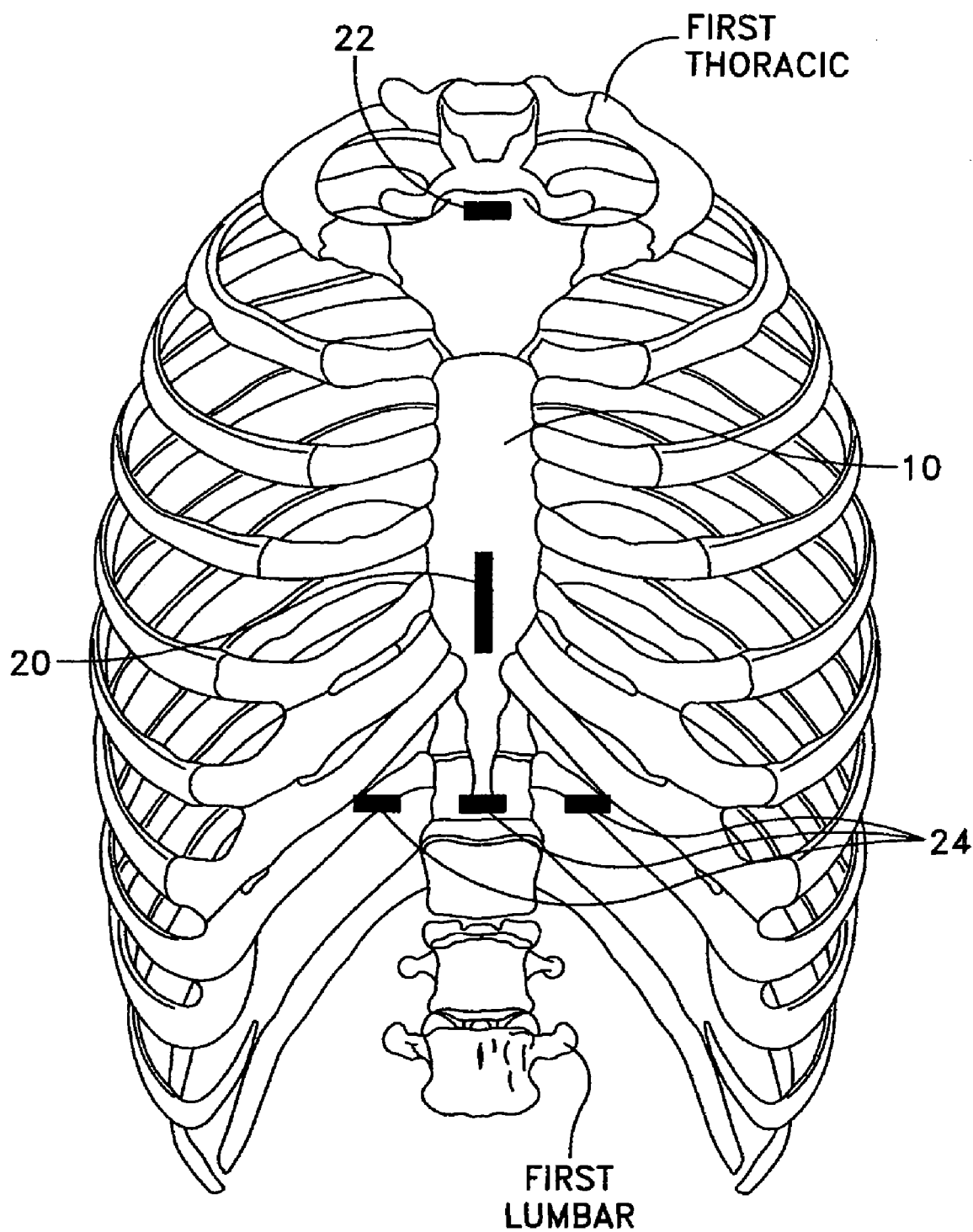
FIG. 2 is a representation of incisions made on a patient pursuant to a method of an embodiment of the disclosure for performing coronary artery surgery.

With reference to FIG. 2, a method according to one embodiment of the disclosure involves making a small incision, in an average size adult patient, of approximately 4-5 cm over the sternum and another cross incision of approximately 2 cm below the sternal notch. This method may be employed to perform pectoralis-sparing, minimally invasive coronary artery bypass surgery. As mentioned above, a first, vertically oriented small incision 20 is made in the lower third of the skin overlying the sternum, approximately 4-5 cm in length (the "working" incision). The first incision 20 is taken down to the level of the sternum 10 and the sternal envelope (investing fascia) is mobilized on the anterior surface using a combination of electrocautery and blunt dissection. The mobilization is carried out laterally with partial mobilization of the pectoralis muscle off of the chest wall. A second, horizontally oriented small incision 22 of approximately 2-3 cm horizontal is made just below the sternal notch (junction of the neck with the chest). This second incision 22 is used initially to help complete mobilization of the aforementioned tissues in the well-known manner. Once mobilization is complete, division of the sternum 10 is accomplished with a standard jigsaw using both incisions.

A mammary retractor may be used through the working incision 20 and below the skin to lift the left and/or right hemi-sternum in order to perform mammary artery pedicle harvesting using standard techniques, but through this small incision. For example, the mammary artery harvest may include adjunctive video assistance. Devices used to perform the method will be discussed in greater detail below with references to FIGS. 4-14.

Figure 3:
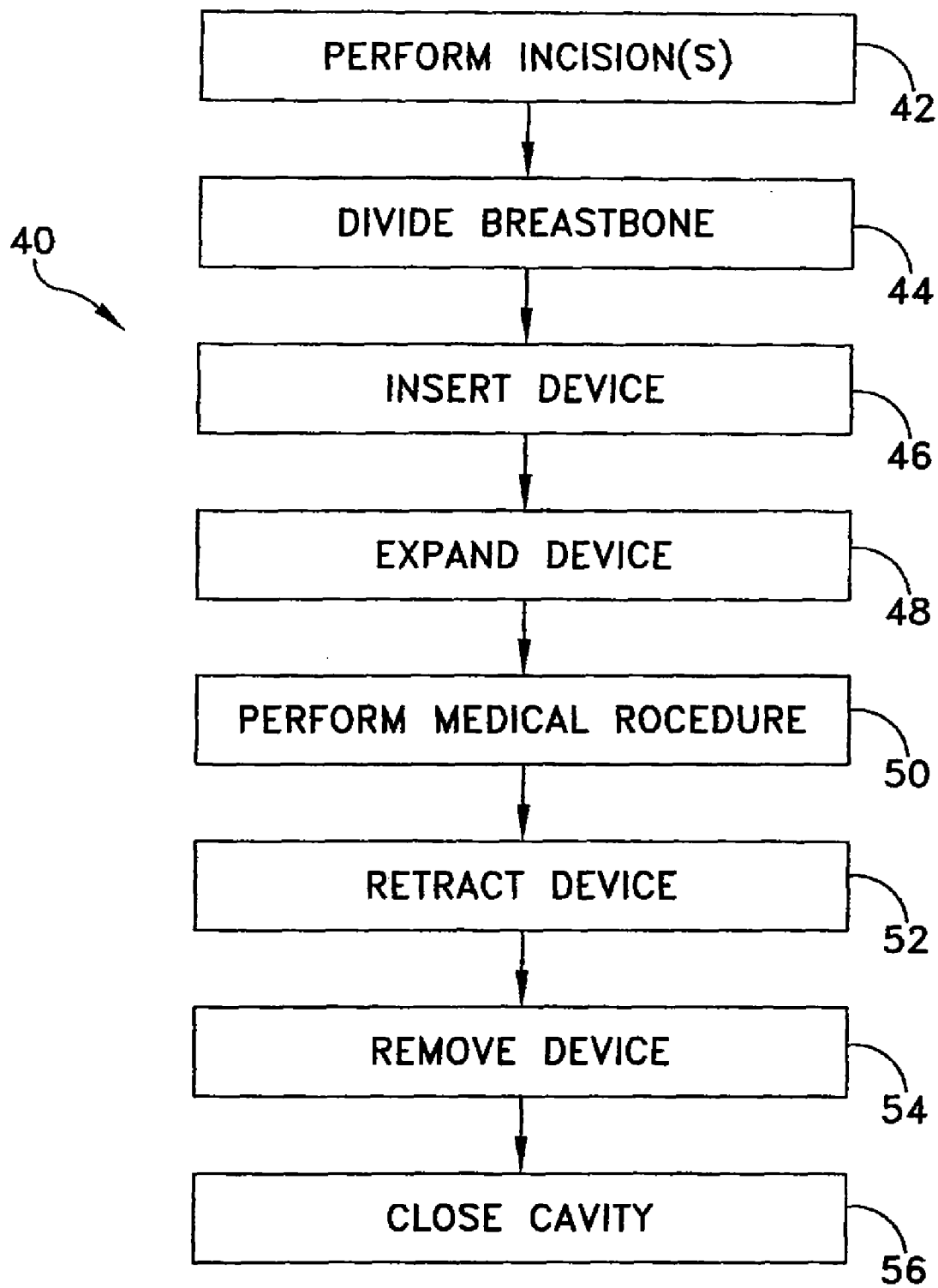
FIG. 3 is a block diagram showing a method of an embodiment of the disclosure for performing coronary artery surgery.

In an embodiment of a method of the disclosure, with reference to FIG. 3, a method of performing coronary artery bypass surgery, generally indicated at 40, is disclosed. A first small incision (e.g., 4-5 cm in length) is made to separate the patient's breastbone. A second small incision (e.g., 2 cm) is made horizontally just below the sternal notch. The incisions are indicated by step 42 in FIG. 3. Once mobilization is complete, the division of the sternum is achieved by standard techniques, e.g., by using a jigsaw (step 44).

A device, such as a retractor of embodiments of the present disclosure, is inserted into the cavity between the divided breastbone, as indicated by step 46 in FIG. 3. The device is manipulated below the skin layer to expand the opening to a distance sufficient to perform a medical procedure, such as coronary artery bypass surgery (step 48). In one embodiment, the breastbone may be expanded up to 20 cm.

Once opened, the medical procedure may be performed (step 50) via the opening. As disclosed herein, the retractor is especially suited for performing coronary artery bypass surgery. However, other procedures are contemplated, and may include, but are not limited to, bypass surgery, valvular and dysrhythmia surgeries and other procedures performed within the chest cavity. It should be understood that the methods and devices disclosed herein, may be applied to perform procedures at other locations within the body, e.g., the thorax or abdomen.

Once the procedure is performed, the device is retracted (step 52) and removed (step 54). At this point, the cavity defined by the opening may be appropriately closed (step 56) by wiring the breastbone and suturing the muscles and skin above the breastbone.

Figure 4A:
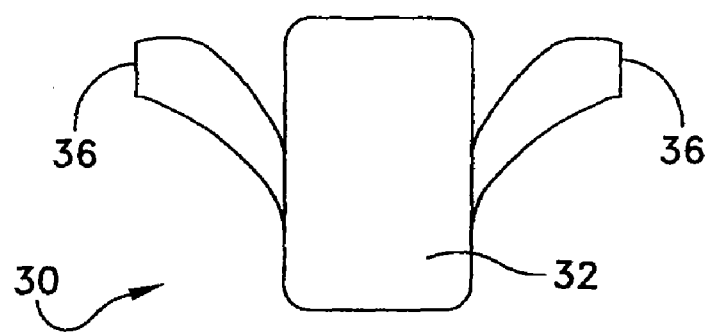
FIG. 4A is a schematic representation of a device of an embodiment of the disclosure for performing a method of coronary artery surgery, with arms of the device being shown in a retracted position.
Figure 4B:
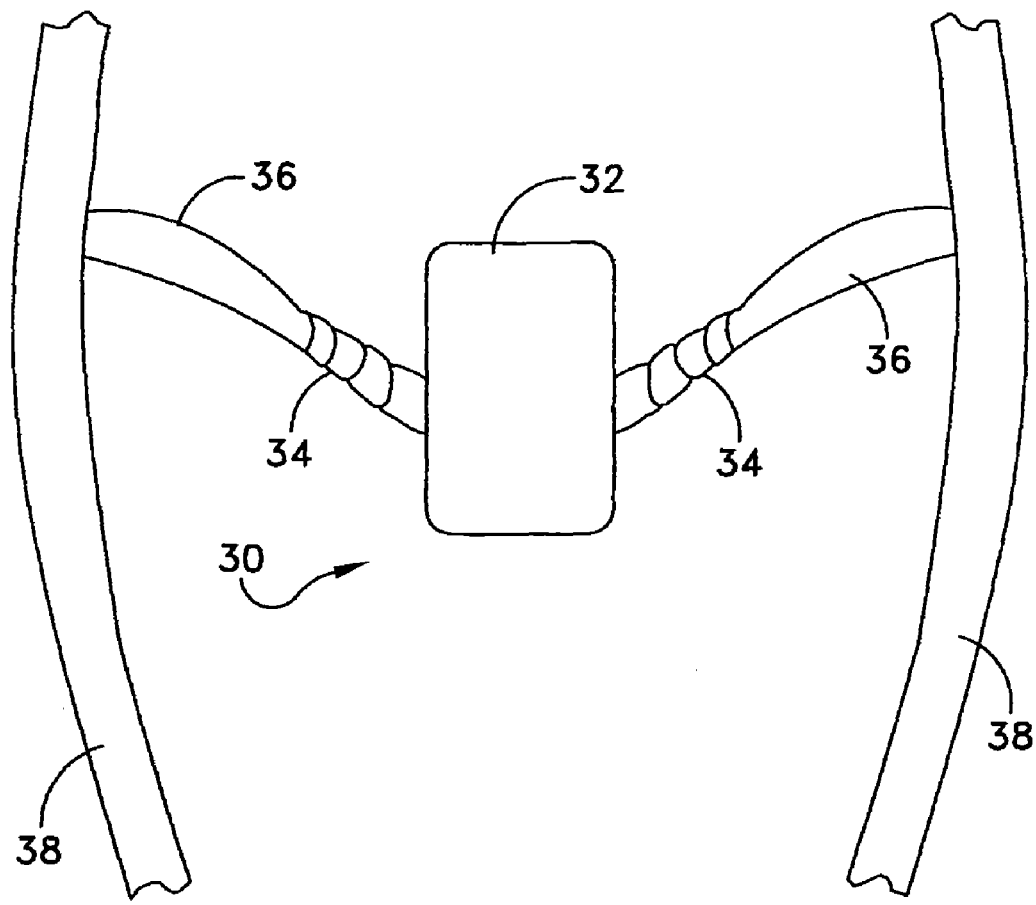
FIG. 4B is a schematic representation of the device shown in FIG. 4A, showing the arms of the device in an extended position.

With reference to FIGS. 4A and 4B, a retractor of an embodiment of the disclosure, generally indicated at 30, is designed so that its mechanism of retraction is under the level of the skin, as opposed to conventional retractors, which are typically placed on top of the sternum, and whose spreading mechanism is above the level of the dermis. A separate crank (not shown) may be placed through a different 1 cm stab incision 24 (FIG. 2) below the main working incision 20 to actuate the spreading mechanism. This stab incision 24 is in the location of one of the typical sites of chest drain placement after coronary artery bypass surgery, and may ultimately be utilized for such a drain. Three or four of these 1 cm stab incisions 24 may be made as illustrated to FIG. 2, all in positions of future drain sites. Once the sternum is spread to the standard width, the formal coronary artery bypass procedure is initiated.

The retractor 30 of an embodiment of the disclosure differs from prior retractors in its operable components are configured to be seated below the level of the dermis, mobilized pectoralis muscle, or the breastbone itself. The retractor 30 is capable of completely separating the breastbone as with prior retractors; however, the low profile of the retractor enables the retractor to be hidden away from the surgical field during the entire surgery.

As shown in FIGS. 4A and 4B, the retractor 30 comprises a central body 32 that may be generally rectangular, circular or oval in shape and sized to fit within the incision performed on the patient's breastbone. With reference to FIG. 4B, the central body 32 houses two telescopic arms, each arm indicated at 34, that extend outwardly from the central body. As shown, one arm 34 is positioned on one side of the central body 32 and the other arm is positioned on the other side of the central body. In another embodiment, a separate device may be provided, e.g., a frame, that houses the telescopic arms. Also, although two arms 34 are illustrated in FIG. 4B, the provision of a device having a central body that engages one side of the opening and one arm that engages the other side of the opening, or a device having more than two arms, e.g., four arms, is contemplated. Provided at the end of each telescopic arm is an end plate 36 that temporarily locks into a platform 38 adapted to conform to the sternal edges or sides of the patient's breastbone. Each platform 38 is approximately 5 cm long and is designed to cup the sternal edge in a longitudinal fashion. In this procedure, the central body 32 of the retractor 30 lies in a plane parallel to, but 1-2 cm below the lowermost plane of the platform 38. Upon extending the telescopic arms 34, the central body 32 is positioned 5-10 cm away from oppositely disposed platforms 38.

In an embodiment of the disclosure, the retractor 30 is adapted to slide into the incision between the divided breastbone. The central body 32 of the retractor 30 will lie below the plane of the sternum, but beyond the bottom of the heart towards the diaphragm, which separates the abdomen from the chest cavity. The dimensions of the central body 32, in one embodiment, may be 2 cm by 2 cm in area from top plan view and be rectangular, circular or oval in shape. Once in position, the sternum is separated by moving the telescopic arms 34 outwardly to engage the end plates 36 to their respective platforms 38. In one embodiment, the end plates 36 temporarily lock in place within grooves (not shown) formed in the platform 38. In this position, a medical procedure, such as cardiac surgery, may be performed. The minimal size of the retractor 30 enables the medical procedure to be performed.

The arrangement is such that when actuating the retractor 30 from above the skin incision, the telescopic arms 34 of the retractor extend and lock in place at a desired width of separation. The telescoping action of the arms 34 is designed to cause the upward angulation of the divided breastbone (up to 45° or more), which provides more volume under the incision for manipulation of the heart.

After the operation is complete, drains and pacing wires are placed. Afterwards, the telescopic arms 34 of the retractor 30 are retracted or withdrawn to within the central body 32 (FIG. 4A) and collapsed to its minimal size by a release mechanism (not shown) built into the central body of the retractor, and the retractor is removed from the patient.

In another embodiment, the device may include a two-part body having opposite edges arced or otherwise configured to engage opposite sides of the divided sternal edges. The device may be manipulated to pull the divided breastbone apart by, for example, a pair of wires that extends through lateral portions of the patient's chest cavity and is ratcheted to each side of the operating table.

In an embodiment of the disclosure, long needle drivers and forceps are used through the working incision. The thymus is divided and pericardium opened, and a pericardial well is created, using long needles that are passed through the skin and underlying muscle. Cannulation sutures are placed through the working incision while Rommel-type tourniquets are brought out through the upper counter incision. The aortic cannula is placed through the upper counter incision and cannulation itself is performed through the working incision. The tourniquets are tightened and the cannula is connected to the heart-lung machine. Venous cannulation is carried out using a long cannula through the common femoral vein in the groin, preferably using a percutaneous Seldinger technique or through the right chest into the atrium in the standard fashion. Cardiopulmonary bypass is established. A retrograde cardioplegia cannula and its tourniquet may be placed through one of the four 1 cm stab incisions (see FIG. 2), and the cannula placed through the working incision and positioned by digital palpation. An antegrade cardioplegia cannula, its tourniquet, as well as the aortic cross clamp may be placed through the upper counter incision. A left ventricular vent and its tourniquet can be placed through one of the stab incisions, and directed through the working incision. The aorta is dissected away from the pulmonary artery and aortic cross clamping/cardioplegia delivery is accomplished.

The heart is then mobilized to perform distal coronary anastomoses. The heart is moved, retracted, and stabilized using deep pericardial sutures or, e.g., sponge stick or other instruments that are brought in through the remaining stab incisions. Laparotomy pads may be delivered through the working incision and placed behind the heart to aid in mobilization. All coronary targets can be visualized through the working incision, and dissection and anastomoses may be carried out in the standard fashion. Once these are completed, proximal anastomoses are performed on the aorta in the usual way, either with the aortic cross clamp in place, or by replacing the cross clamp with a partial aortic clamp through the upper counter incision. Weaning from cardiopulmonary bypass and decannulation are completed. After hemostasis is ensured and drains are placed (and brought out through the stab incisions), the sternum is re-approximated with standard sternal wires through both the working and upper incisions. The upper and working incisions are closed with absorbable suture in layers.

As can be appreciated, the provision of smaller incisions results in improved aesthetics and less post-operative pain. Smaller incisions may significantly diminish the amount of pain associated with movement, ambulation, coughing and deep breathing. Smaller incisions may also lead to decreased atelectasis (lung segmental collapse) and pleural effusions, and other pulmonary complications. The aforementioned benefits would likely contribute to a shorter hospital stay and less reliance on health care benefits. Post-operative recovery may be significantly hastened, and resumption of full activity might be decreased to approximately 1-2 weeks from 4-6 weeks. Restrictions on activity may be lightened, because the pectoralis muscle complex has been mobilized off of the chest wall, and there will be significantly less force placed on the sternal (bone) closure. This may also potentially lead to a lower risk of sternal dehiscence (separation). As might be appreciated, based on the disclosure herein, some (but not all) embodiments of the present disclosure can address or assist with respect to one or more of the above advantages.

Unknown beneficial attributes of the mesothelial cell lining of the heart and its associated tissues may be protected due to preservation of high levels of humidity because of the minimally invasive approach. Benefits may include less post-op adhesion formation (scarring) that would make re-operative cardiac surgery less risky. Similar benefits have been witnessed after laparoscopic and video-assisted thoracic surgeries. The prevention of desiccation (drying out) of these tissues may have a beneficial effect on the incidence of post-op atrial fibrillation (a heart rhythm disturbance that occurs in one-third of post-op cardiac patients and carries significant cost and morbidity). As might be appreciated based on the disclosure herein, some (but not all) embodiments of the present disclosure can address or assist with respect to one or more of the above advantages.

Figure 6:
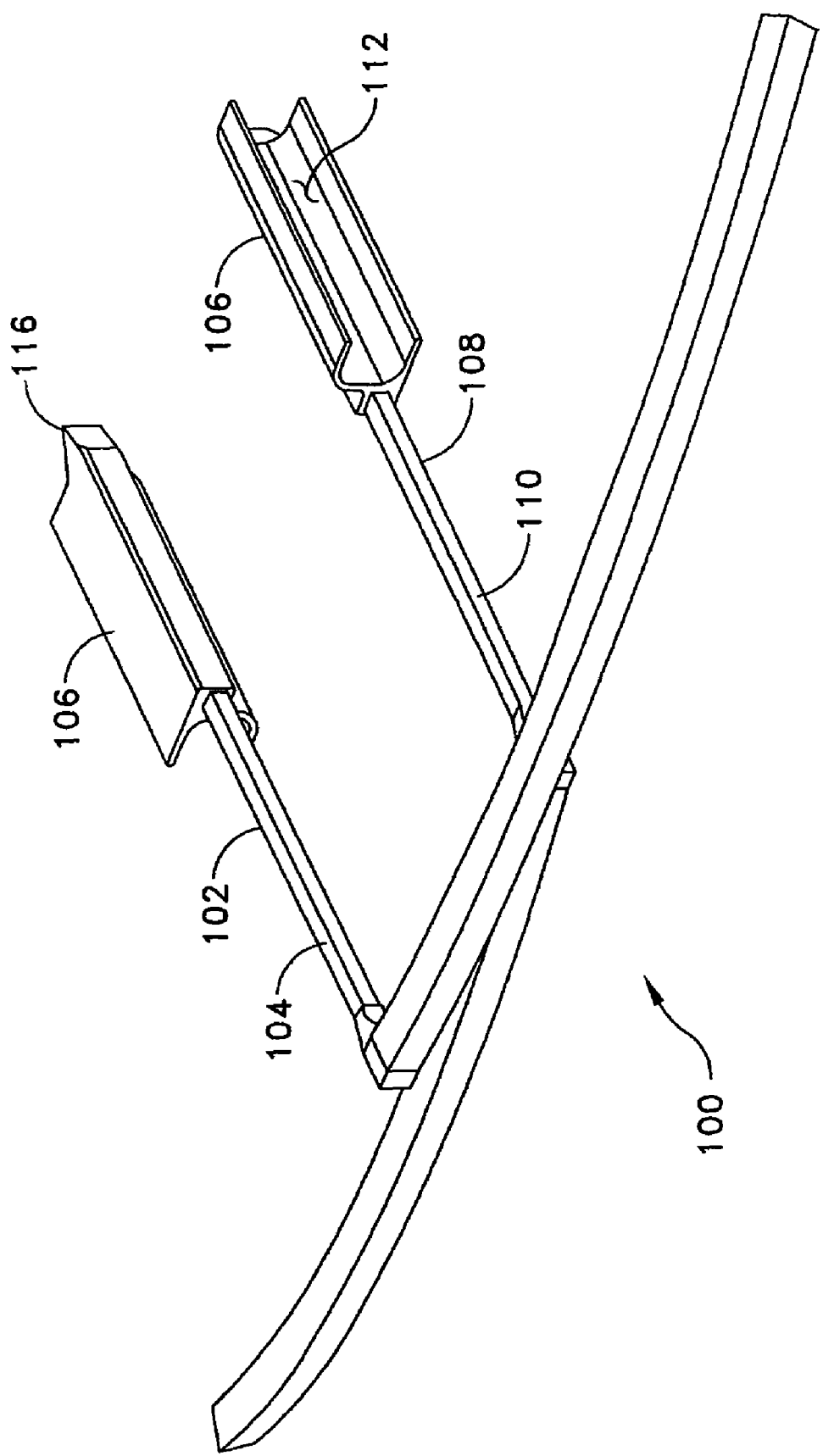
FIG. 6 is a perspective view of the device shown in FIG. 5, showing the arms of the device in an extended position.

Turning now to FIGS. 5 and 6, there is generally indicated at 100 a device of an embodiment of the disclosure for expanding an opening under the skin layer of a patient so that a medical procedure, such as cardiac bypass surgery, may be performed. As discussed above, the device 100 is configured to fit within and open a small incision (e.g., 4-5 cm in length) made to separate the patient's breastbone. The device may also be used to widen other openings formed in the patient, such as openings between the patient's ribs. The device includes a first arm 102 having a distracter shaft 104 and a support channel 106 that is releasably attachable to the distracter shaft 104. The device 100 further includes a second arm 108 having a distracter shaft 110 and another breastbone support channel 106 that is identical to the breastbone support channel 106 used on the first arm 102. The support channels 106 are configured to engage opposite sides of the opening of the patient (e.g., the left and right hemi-sternums). As shown in FIG. 5, the first and second arms 102, 108 may be positioned in a retracted position in which the arms are adjacent one another. In one embodiment, the first arm 102 may be configured to overly the second arm 108. FIG. 6 shows the first and second arms 102, 108 in an extended position so as to expand the opening by spreading the left and right hemi-sternums.

Figure 7:
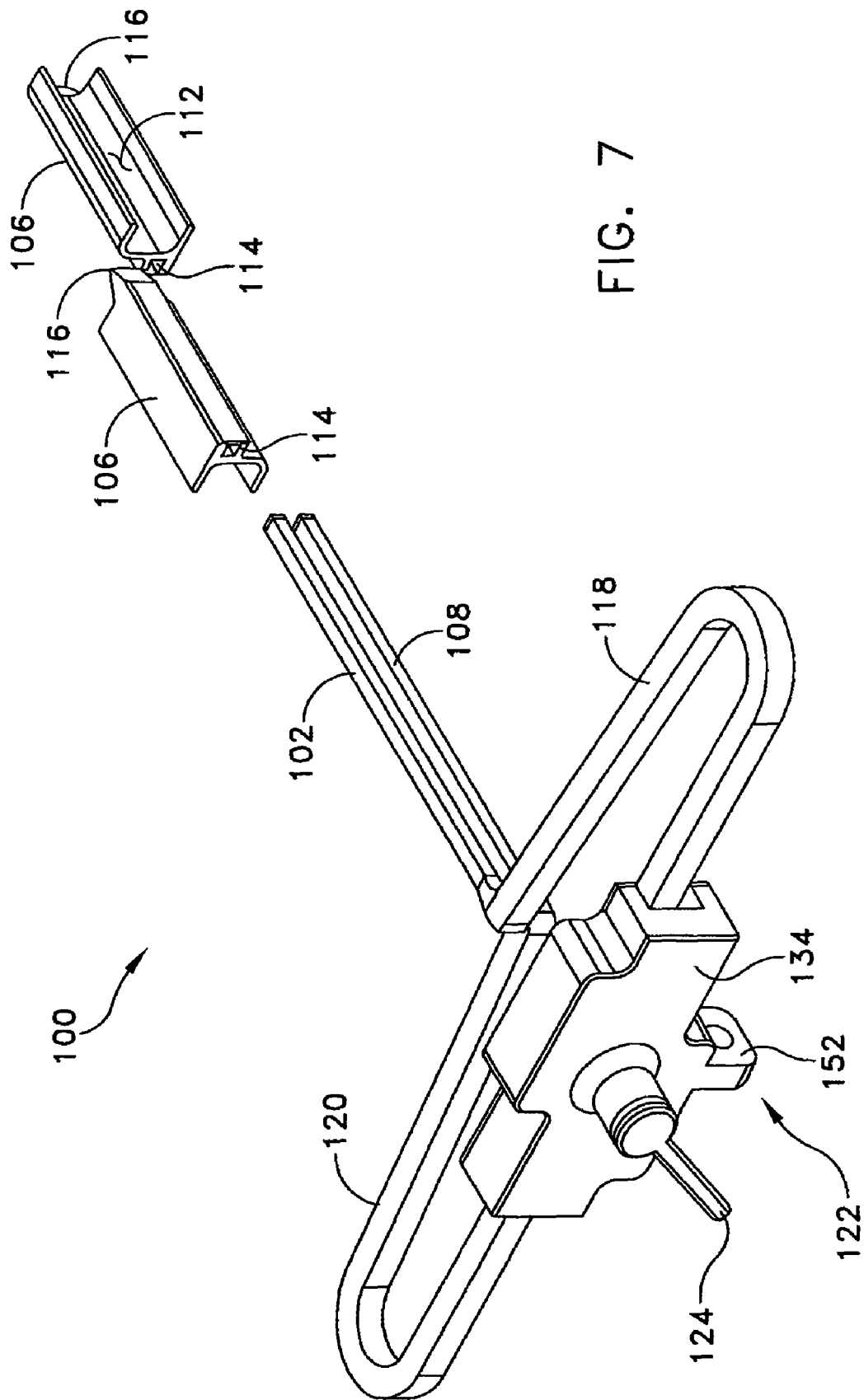
FIG. 7 is a perspective view of the device shown in FIGS. 5 and 6, with a operating mechanism being attached to actuating arms of the device and breastbone support channels being unattached to distracter shafts of the device.

In one embodiment, each support channel 106 includes a C-shaped surface 112 that is configured to engage the patient's divided breastbone under the skin layer. Although described to engage a patient's breastbone, the C-shaped surface 112 may be configured to engage other body tissue, such as a patient's rib. Referring to FIG. 7, each support channel includes an elongate opening 114 formed therein, and is attached to its respective arm 102 or 108 by sliding the distracter shaft 104 or 110 of the arm through the elongate opening. As shown, each support channel 106 includes a wedge-shaped leading edge or nose 116, which generates a dividing effect in distracting the breastbone. In a certain embodiment, the support channel 106 is approximately 5 cm long so as to fit within the opening of the patient.

Figure 8:
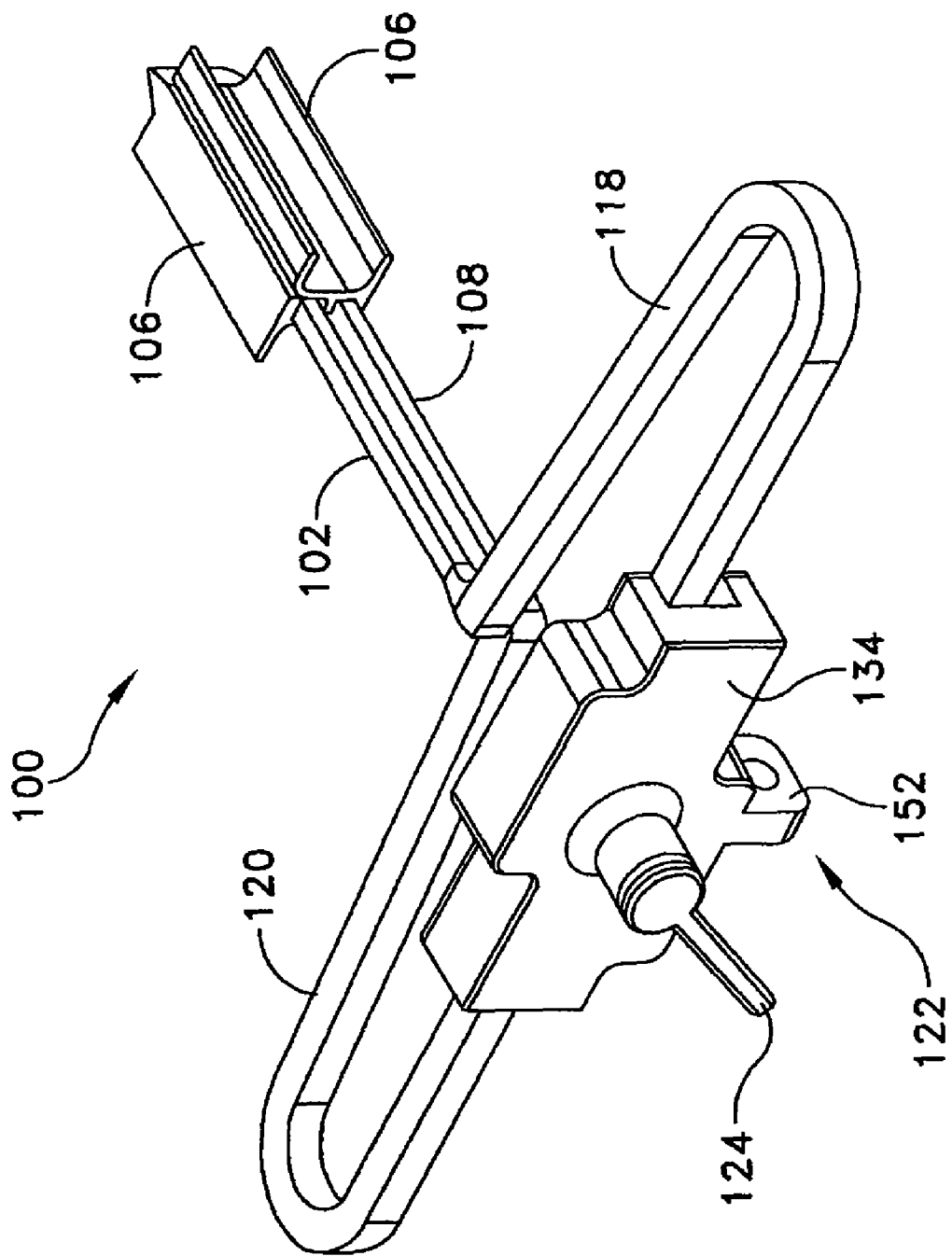
FIG. 8 is a perspective view of the device shown in FIG. 7, showing the breastbone support channels being attached to the distracter shafts and in a retracted position.
Figure 9:
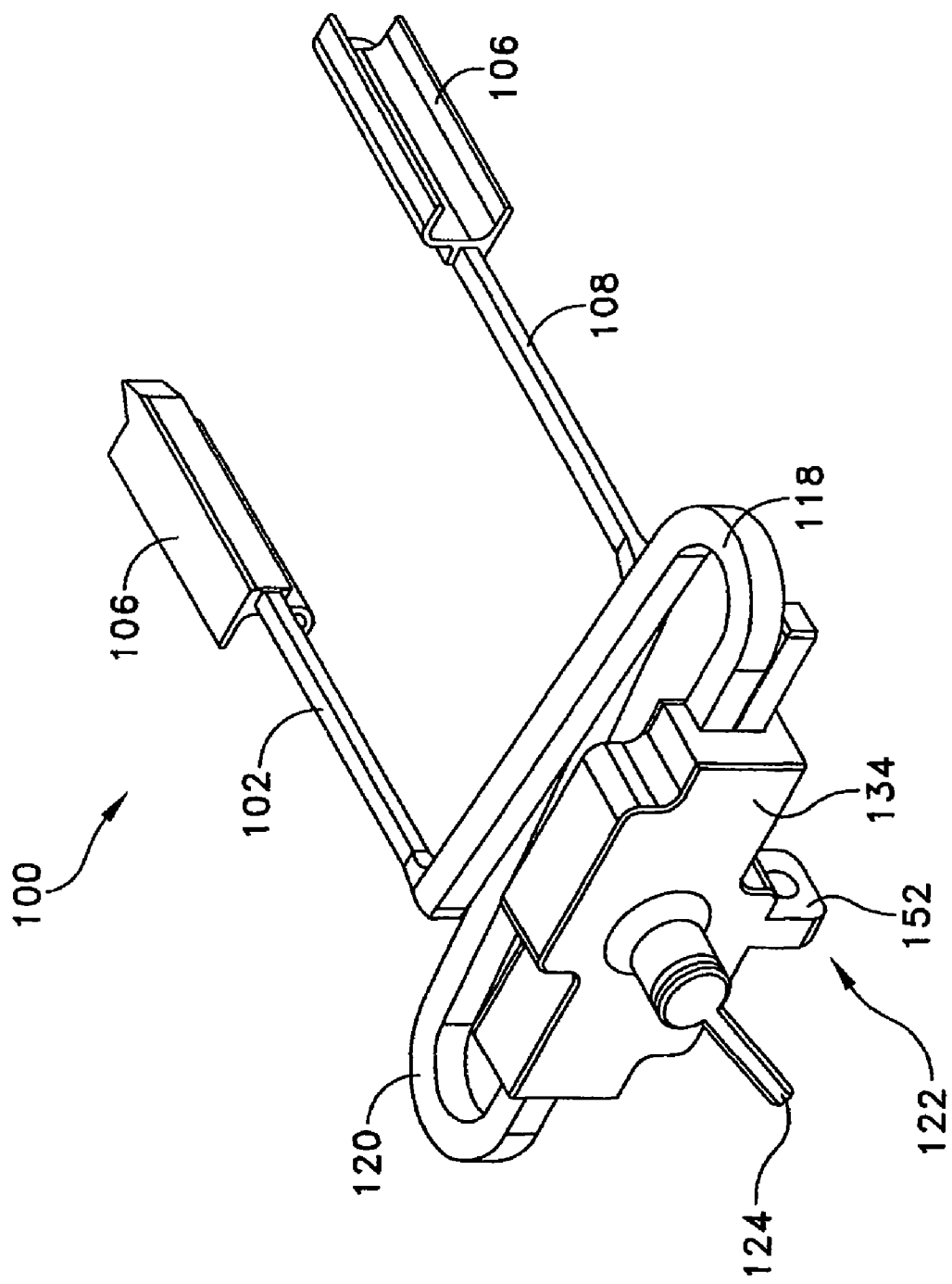
FIG. 9 is a perspective view of the device shown in FIG. 8, with the arms of the device being shown in an extended position.

Referring now to FIGS. 7-9, and more particularly to FIGS. 8 and 9, the first arm 102 is connected to a first actuator member 118 and the second arm 108 is connected to a second actuator member 120. Each actuator member 118, 120 is generally a U-shaped structure. The free ends of the actuator members 118, 120 are coupled to a spreader mechanism, generally indicated at 122, which are adapted to move the actuator members 118, 120 with respect to each other. Specifically, the spreader mechanism 122 is configured to move the first and second arms 102, 108 via respective actuator members 118, 120 between a retracted position in which the arms are positioned next to one another and an extended position in which the arms move away from each other. In other embodiments, the spreader mechanism 122 may be configured to move only one arm, e.g., first arm 102, with the other arm, e.g., second arm 108, being fixedly attached to the spreader mechanism. FIG. 8 shows the first and second arms 102, 108 in their retracted position. FIG. 9 shows the first and second arms 102, 108 in their extended position. A suitable device, such as a hand crank 124, may be provided to move the first and second arms 102, 108 between their retracted and extended positions. In other embodiments, an automated mechanism may be employed, such as a motorized system, to move the first and second arms 102, 108. In one embodiment, the extended position may widen the opening underneath the skin layer up to 20 cm, or more without tearing or otherwise harming the skin and muscle layers.

Figure 10:
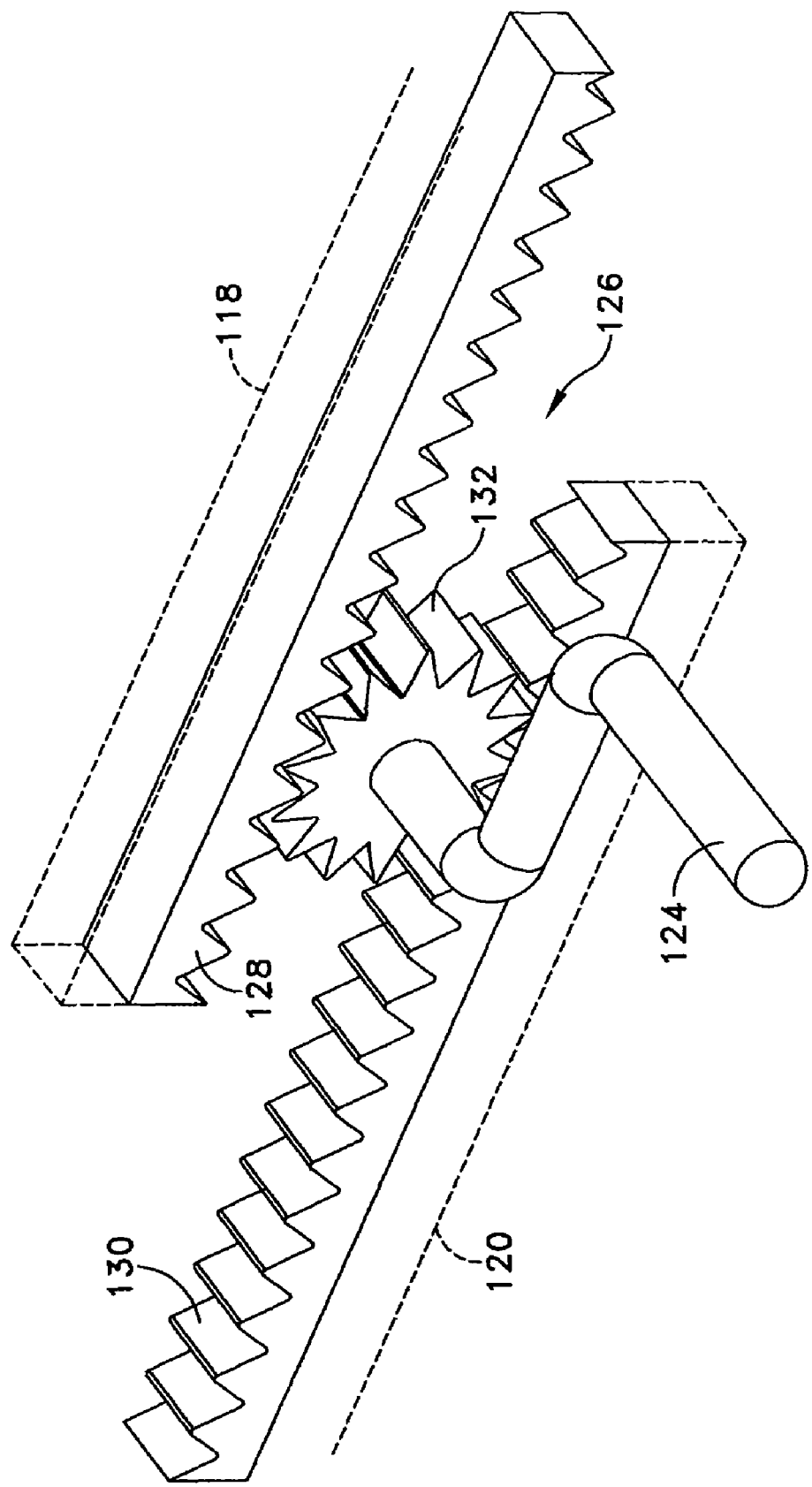
FIG. 10 is a perspective view of a gear box of the operating mechanism shown in FIGS. 7-9.

Turning now to FIG. 10, a gear mechanism, generally indicated at 126, is provided to move the first and second arms 102, 108 between their retracted and extended positions. As shown, the gear mechanism 126 includes a first gear segment 128 attached to the first actuator member 118. Similarly, a second gear segment 130 is attached to the second actuator member 120. A gear wheel 132 is suitably positioned between the first and second gear segments 128, 130. The gear wheel 132 is connected to the hand crank 124 so that upon rotating the hand crank, the gear wheel rotates. The arrangement is such that by rotating the hand crank 124, the first and second gear segments 128, 130 move the first and second actuator members 118, 120. With the arrangement illustrated in FIG.

10, by rotating the hand crank 124 in a clockwise direction, the first and second arms 102, 108 move to their retracted position. By rotating the hand crank 124 in a counterclockwise direction, the first and second arms 102, 108 move to their extended position. A suitable casing 134 (shown in FIGS. 7-9) is provided to house the components of the gear mechanism 126.

Figure 11:
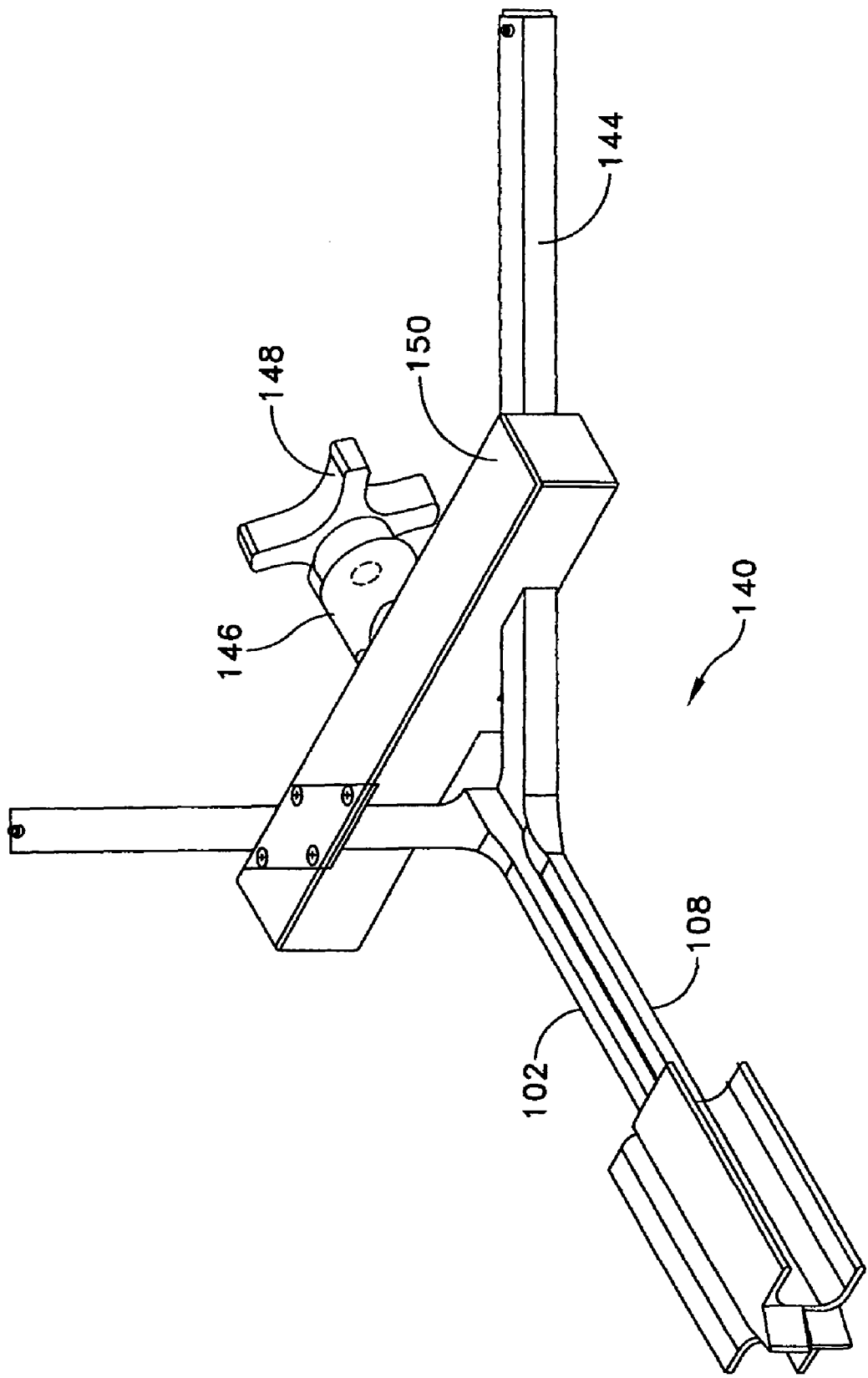
FIG. 11 is a perspective view a device of yet another embodiment of the disclosure for performing a method of coronary artery surgery, with arms of the device being shown in a retracted position.
Figure 12:
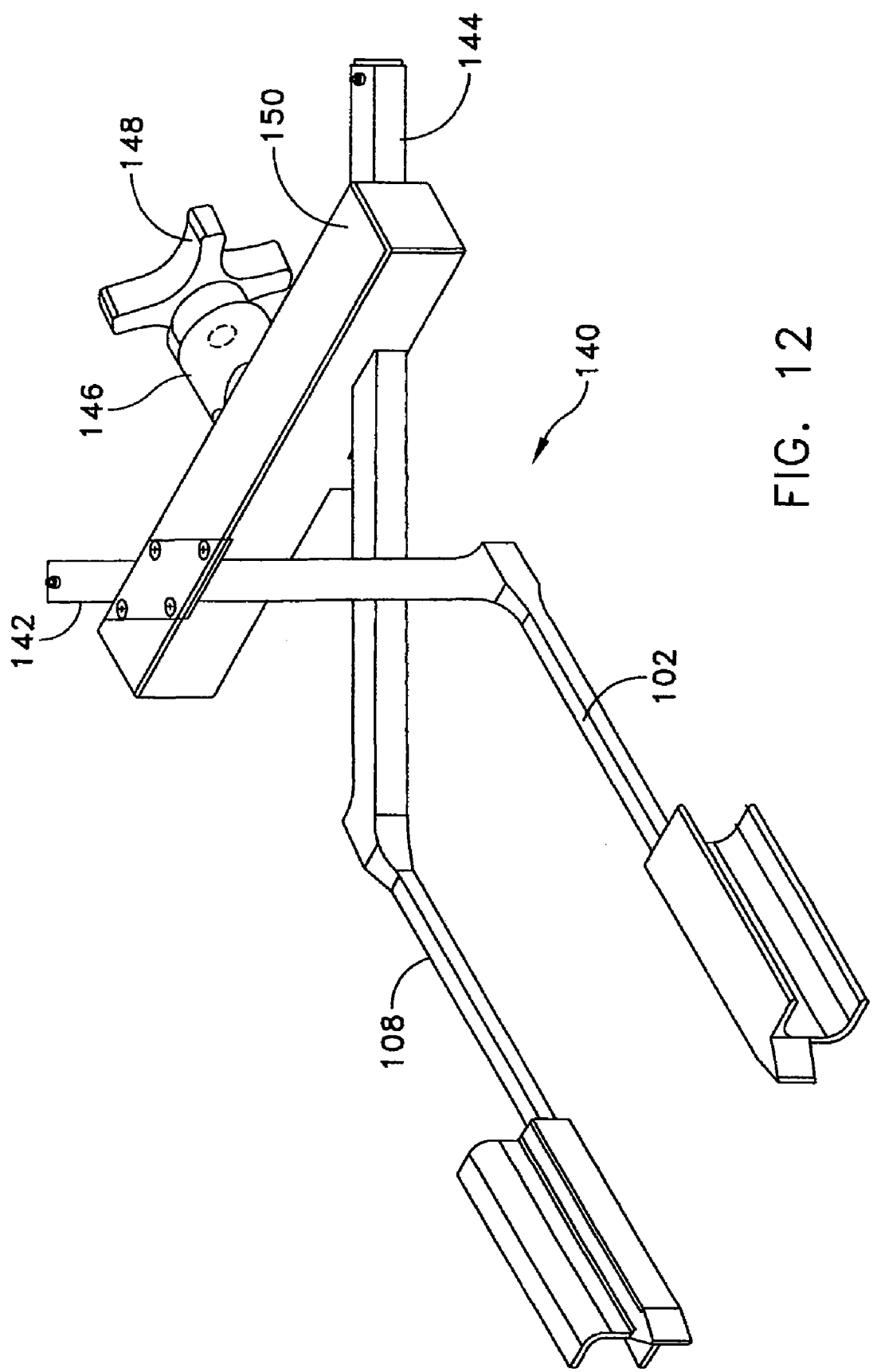
FIG. 12 is a perspective view of the device shown in FIG. 11, showing the arms of the device in an extended position

FIGS. 11 and 12 illustrate a device, generally indicated at 140, of another embodiment of the disclosure. As shown, the first and second arms 102, 108 of the device 140 are configured to be identical to the first and second arms 102, 108 of device 100. Device 140 includes straight actuator members 142, 144, that are connected to first and second arms 102, 108, respectively, and a spreader mechanism 146 designed to move the first and second arms 102, 108 via actuator members 142, 144 between retracted and extended positions. As shown, the spreader mechanism 146 is a scissor-type mechanism in which a knob 148 is provided to move the first and second arms 102, 108. FIG. 11 shows the first and second arms 102, 108 in their retracted position. FIG. 12 shows the first and second arms 102, 108 in their extended position to widen the opening. A casing 150 is provided to enclose the components of the spreading mechanism 146.

During use, a device, such as device 100 or 140, may be disposed over the patient so that the arms of the device are positioned underneath the patient's skin layer and the spreader mechanism is disposed above the patient. Since the spreader mechanism is located at one end of the device, the first and second arms, when moved to their extended position, enable the surgeon to view the cavity directly through the opening. A primary benefit of designing the support channels to engage tissue below the skin layer (e.g., the patient's breastbone) is that the incision can remain small (e.g., 5 cm). It is certainly contemplated, as witnessed by the embodiment of the device 30 shown in FIGS. 4A and 4B, the spreader mechanism (i.e., central body 32) may be disposed within the opening under the skin layer. However, the surgeon, when employing this type of device, must work around the spreader mechanism.

Figure 13:
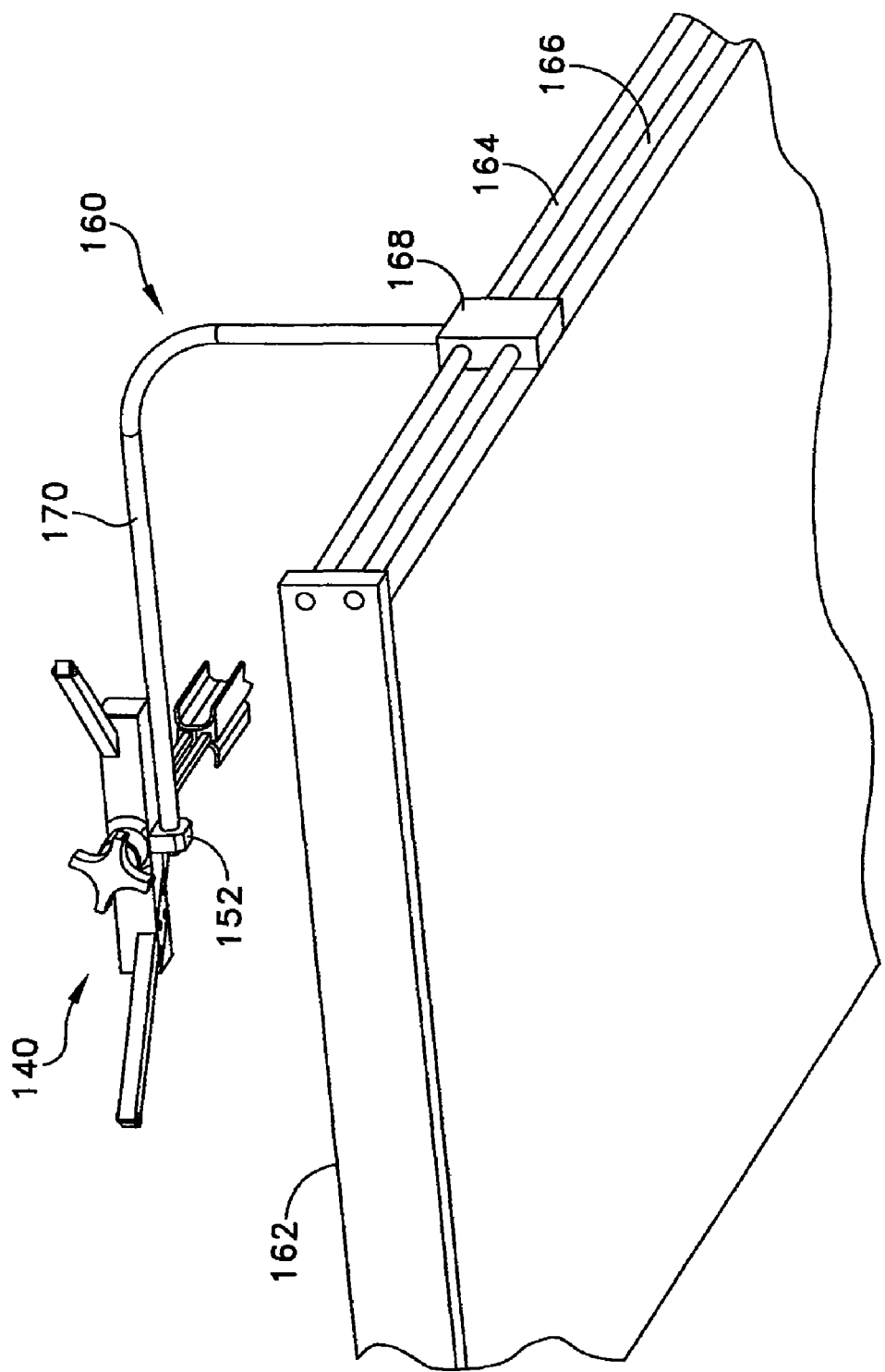
FIG. 13 is a bottom perspective view of the device shown in FIGS. 11 and 12 showing the device mounted on a support assembly.
Figure 14:
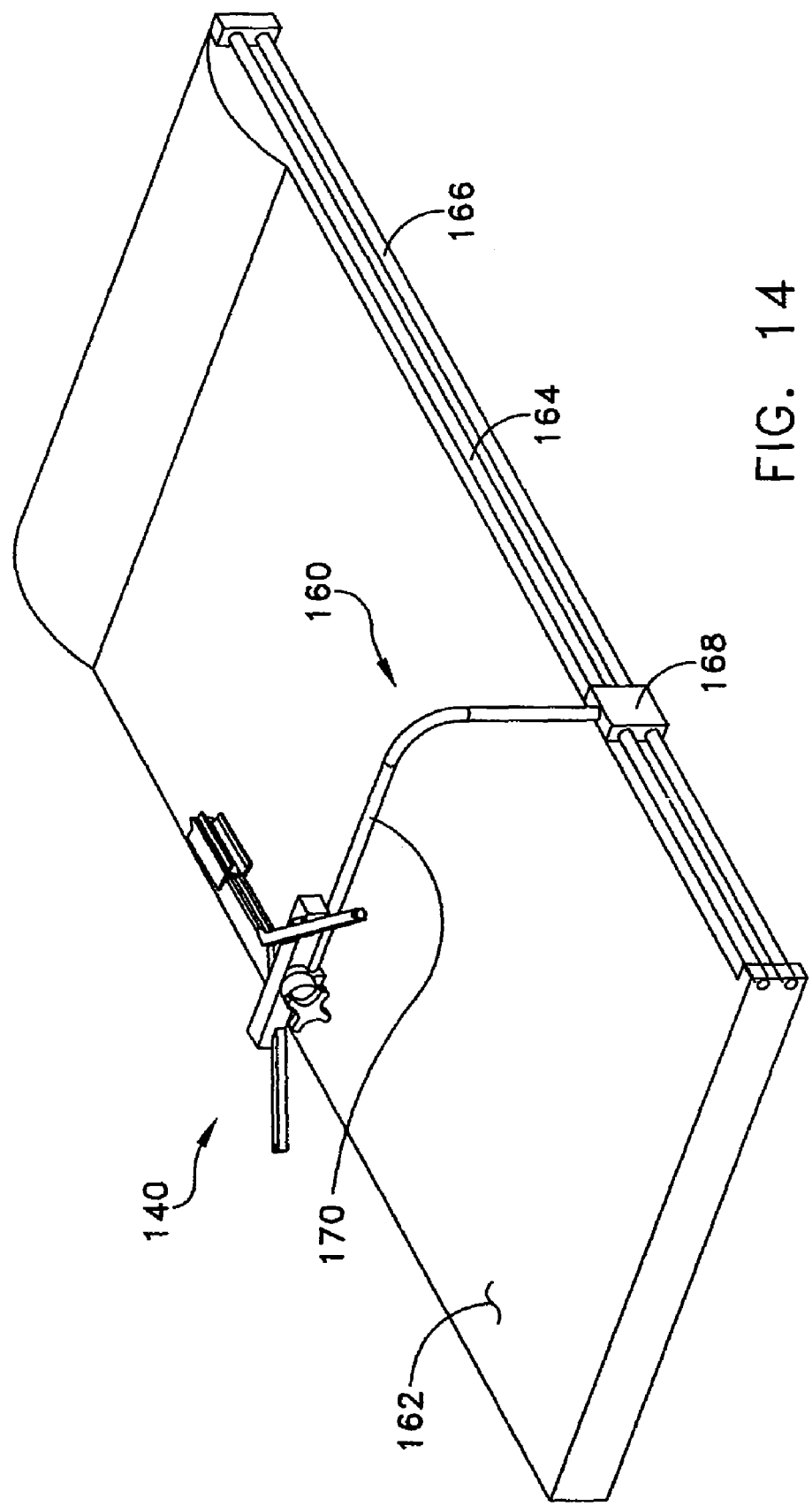
FIG. 14 is a top perspective view of the device shown in FIG. 13.

In one embodiment, the device 100 or 140 may include a mount 152 formed on the spreader mechanism 122 or 146 to mount the device on a support assembly. As shown, such a mount 152 is provided on the underside of the spreader mechanisms 122, 146. FIGS. 13 and 14 illustrate a support assembly, generally indicated at 160, that is integrally formed as part of an operating table 162. As shown, the operating table 162 includes a pair of rails 164, 166 and a slider 168 that is designed to slide along the lengths of the rails. A locking mechanism (not shown) may be provided to lock or otherwise secure the slider 168 in place. A support arm 170 is attached at one of its ends to the slider 168, the support arm 170 being configured to extend over the operating table 162 so that it is positioned above the patient. The other end of the support arm 170 is inserted into or otherwise connected to the mount 152 to secure the device 100 or 140 to the support arm. The arrangement is such that the device 100 or 140 may be slid along the length of the rails 164, 166 to position the device at any position over the patient. The support arm 170 may be telescopic, for example, so that the device 100 or 140 may be moved laterally with respect to the patient. Although FIGS. 13 and 14 illustrate the device 140, it should be understood, based on the foregoing description, that device 100 may be secured to the support arm 170 as well via mount 152.

In one application using the device, an access incision is created over the lower third of the breastbone longitudinally, and through it, tissues are dissected and the breastbone is completely divided with a standard jigsaw. As discussed, the device is modular in construction, and, in one embodiment, includes support channels with the C-shaped surfaces that are configured to contact and divide the breastbone. Reference may be made to FIG. 15, which illustrates the two support channels 106 engaging a divided breastbone 180 below the skin layer 182. In one embodiment, the support channels 106 are between 5 and 12 centimeters long. Two of these support channels, one for each hemi-sternum, are inserted into the access incision, and are directly applied to the split breastbone 180 longitudinally. As described with reference to devices 100 and 140, the remaining part of the device has long slender distracter shafts. With the device in the retracted, non-deployed position, the distracter shafts are inserted into a surgically created drain site or sites below the access incision and advanced to engage the two breastbone support channels. In this embodiment, the leading edges of these channels are pointed to allow for a wedge effect in distracting the breastbone 180. The distracter shafts are connected to the actuator arms, which, depending on the device, may be straight, curved, or of any other shape. The actuator arms are driven by the spreader mechanism that has a gear box provided in a casing or housing. The gear box in this example may be hand powered by a hand crank or a fluted thumb knob. In other embodiments, any suitable ergonomic device may be provided to allow the operator to distract the support channels with minimal effort. Integral with the casing of the spreader mechanism may be low friction guide shoes that allow either the actuation arms to pass through with low friction. There may be further provided assembly covers for the actuator arms to prevent trauma to the skin layer.

In certain embodiments, it is envisioned that the mount 152 may be adjunctively provided to enhance efficiency of the device. In one embodiment, the mount 152 affixes the device to the operating table 162 by securing the device to the support arm 170, which is slidably mounted on the operating room table by slider 168. This arrangement is designed to stabilize the device as the split breastbone 180 is distracted or separated. The mount 152 is designed to permit mobilization and fixation of the device at differing angles from its insertion angle. This configuration is intended to offset discrepancies in the angle at which the divided breastbone 180 is spread due to asymmetries in either the device or in the patient's body. In addition, the mount 152 may have further attachments to expand the device's capabilities to provide sites of fixation for stabilizing devices for beating heart surgery, or for hardware designed to distract the access incision to place it over different areas of interest and facilitate surgery, for example.

It is envisioned that a fiber optic carrier (e.g., cabling) may be incorporated into the actuator arms, and contiguously through the distracter shafts so that they may engage a light delivery system built into the breastbone support channels. This construction enables the surgical field to be lit from within opening, as opposed to directing light from outside the incision towards the deeper surgical field.

Similarly, video channeling or cabling may be built into the same above structures, with a video camera built into one or both the breastbone support channels to allow for live video of the surgical field for assistance during surgery or for recording and editing purposes. It this example, hardware for both light and/or video probes would attach to an appropriate portion of the actuation arms from a source off of the operating room table, as is done commonly for standard videoscopic procedures. In an alternate embodiment, the light and video optic cable could be connected to the breastbone support channels directly (without channeling through the actuator arms and distracter shafts, possibly through a one of the drain site incisions or another separate counter-incision.

In addition, separate hollow channels bored contiguously through the actuation arms and distracter shafts could be used for delivering sterile gas, such as carbon dioxide ($CO_2$), deep into the surgical field from a source off of the operating table, for example. $CO_2$ may be used in open heart surgery to displace air, as $CO_2$ is readily absorbed in blood, and air can cause "gas embolism," with undesirable consequences. Directed blasts of CO2 can also be used to displace blood from surgical areas of interest during coronary surgery, for example.

FIGS. 16 and 16A show a nested configuration of a device having two L-shaped actuators 118, 120, which are attached to arms 102, 108, respectively. The arms 102, 108 may be fixed to, or reversibly attached to support channels 106. A spreader mechanism 146, which may embody one or more gears that are driven in a rack-and-pinion fashion, drives the movement of the actuators 118, 120 to spread the arms 102, 108 apart to an extended position. As shown, each actuator 118, 120 includes teeth provided on one side of the actuator to engage gears of the spreader mechanism. In a retracted (closed) position, the arms 102, 108 and the actuators 118, 120 are configured such that they form one L-shaped member that is adjacent to and positioned within a second L-shaped member, when viewed in FIG. 16. It should be understood that although both actuators 118, 120 are coupled to the spreader mechanism 146 to move the arms 106, 108 apart from one another, the spreader mechanism may be configured to drive the movement of one actuator (118 or 120) with the other actuator being fixed to the spreader mechanism or some other support. In such an embodiment, only one actuator (118 or 120) would require teeth formed on the side of the actuator.

FIG. 17 shows another embodiment of a device having arms 102, 108 that are attached to actuators 118, 120 respectively. As shown, a segment 184 of one of the arms (arm 108) overlies actuator 118. It should be understood that a segment of one of the arms may be configured to underlay an actuator in other embodiments of the device.

Figure 18:
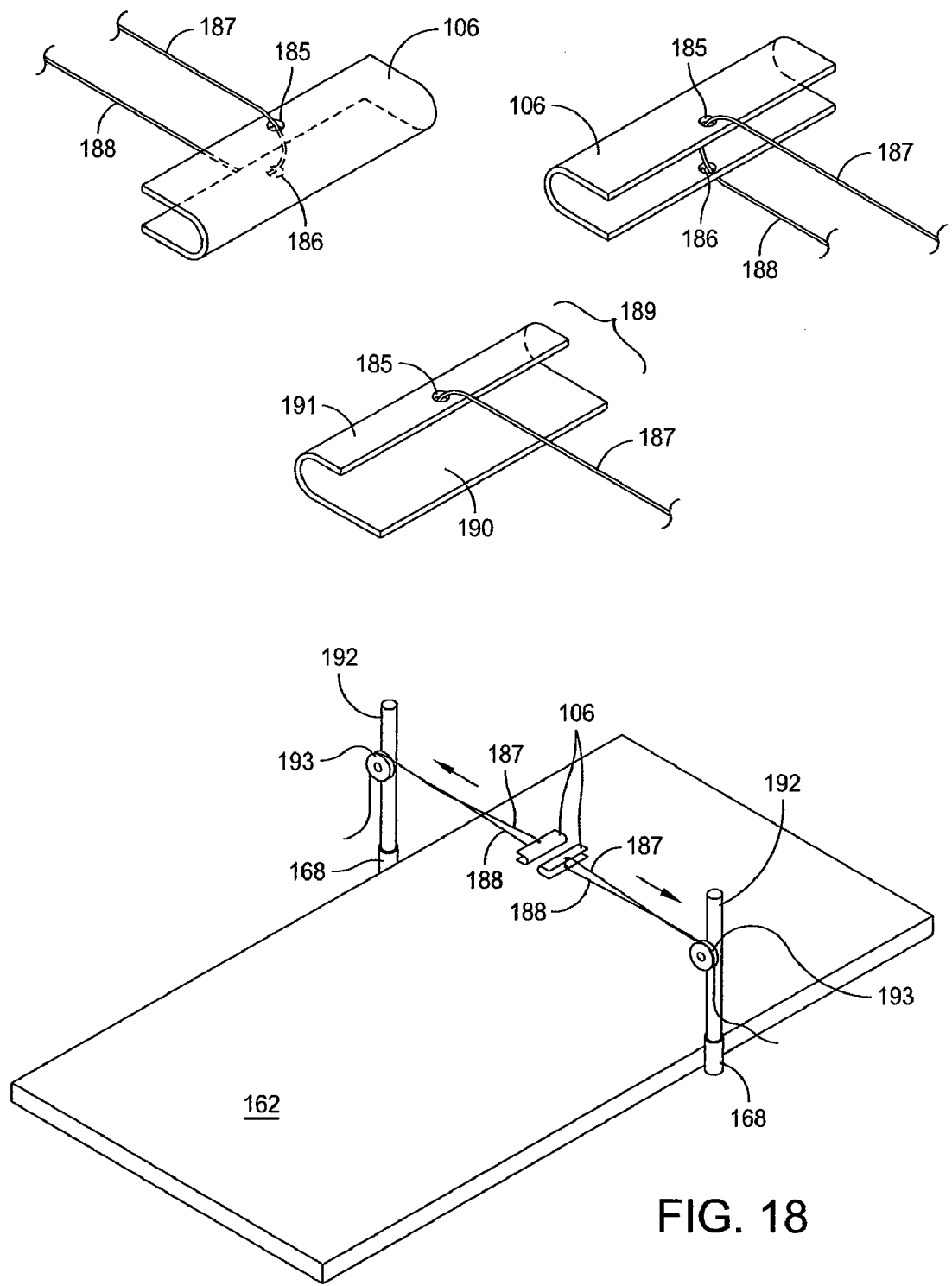
FIG. 18 is a perspective view of an embodiment of a device showing two spreader mechanisms attached to opposite sides of an operating room table that operate two winches.

FIG. 18 illustrates another embodiment of a device having a double spreader mechanism design. As shown, the device includes two spreader mechanisms, each indicated at 193, attached to opposite sides 168 of an operating room table 162 by a support bracket 192. In one embodiment, each spreader mechanism 193 in this iteration is a pulley, which are attachable to cables 187, 188. Alternatively, the spreader mechanism may be configured to operate only one cable. Cables 187, 188 are attached to or reversibly attached to one or more locations 185, 186 provided on the support channels 106. A different support channel 189 may be provided that has a wide portion 190 and a narrow portion 191, which may be advantageous to this design to prevent slippage from the divided breastbone edge while the pulley mechanism is actuated.

FIGS. 19 and 19A show another embodiment of a device that is meant to be placed completely underneath the skin layer when a tissue plane and space is developed between adjacent muscle and subcutaneous fatty tissue. Arms 102, 108 are either reversibly attachable to support channels 106 or permanently attached to support channels 194. Arm 102 is attached to a base 195, which has an opening 196 configured to have an internal thread so as to threadably receive (in a nut-and-bolt fashion) a threaded actuator 197. Arm 108 is connected at one end 202 to the actuator 197. The end 202 of the arm 108 includes a freely spinning washer (not shown) so that when the actuator 197 is turned by a crank 201, the arm 108 is not turned in conjunction with the actuator. Instead, turning the actuator 197 by using the crank 201 causes the arms 102, 108 to extend apart from one another in a common (e.g., horizontal) plane. The actuator 197 may be larger than ¼-inch in diameter in order to accommodate the load required for spreading apart resistant tissue. The crank 201 may have a joining tip 200 that fits into a socket 199 of the actuator bolt head 198. When the crank 201 is turned in the opposite direction, the arms 102 and 108 are retracted back to a collapsed position. Typically, with the device completely underneath the skin layer, crankshaft 201 is placed via a separate stab incision (such as stab incision 24 shown in FIG. 2) in order to join the tip 200 and the socket 204 in order to actuate the device and spread the arms 102, 108 apart underneath the skin layer.

Figure 20A:
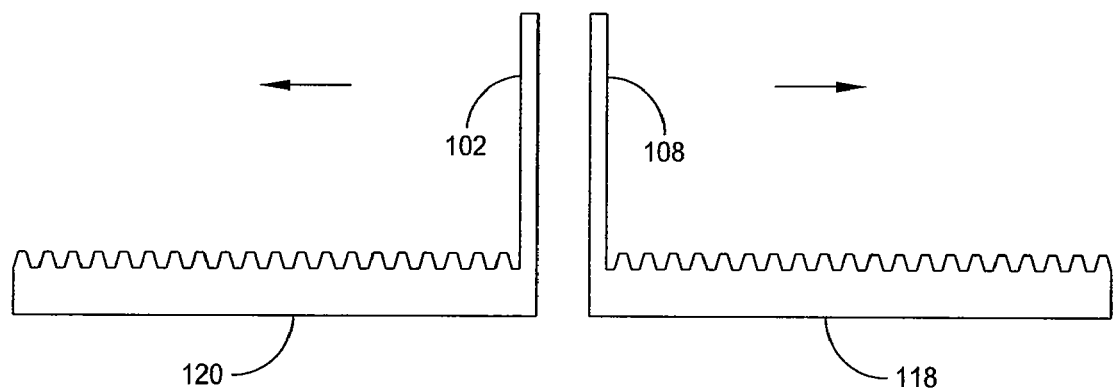
FIGS. 20 and 20A are exploded perspective views of another embodiment of a device having two spreader mechanisms that are attached to opposite sides of an operating room table utilizing a rack-and-pinion mechanism to spread arms of the device apart.
Figure 20:
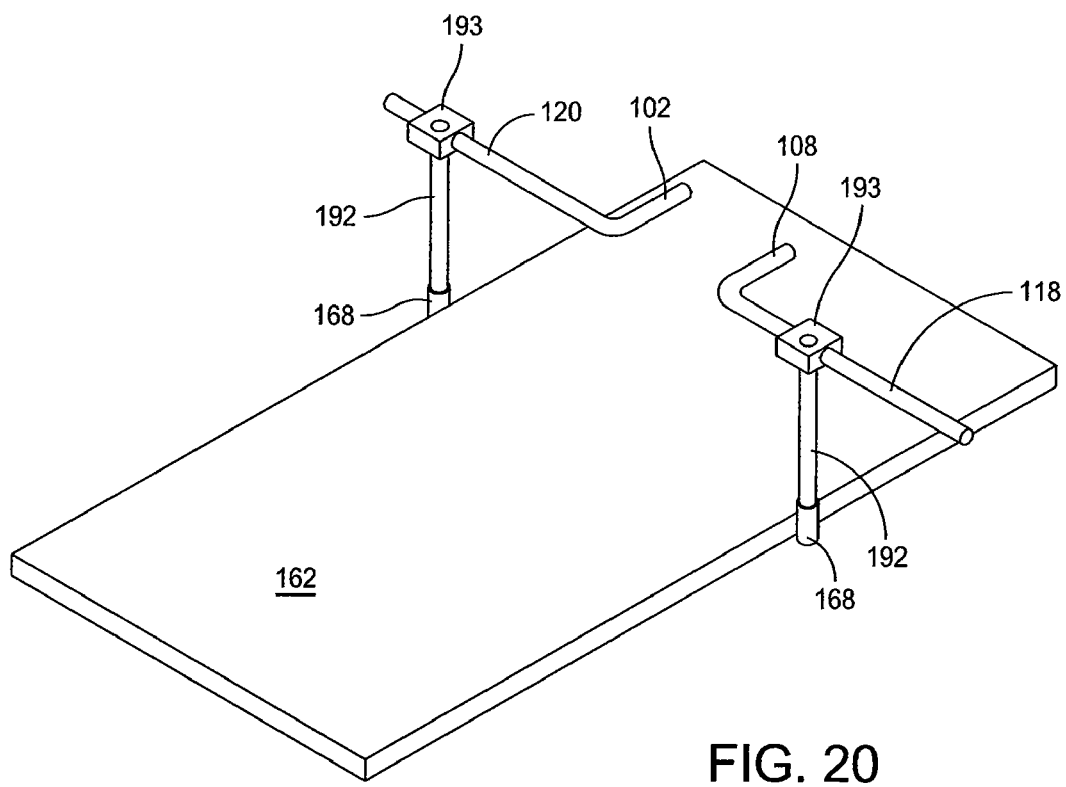

FIGS. 20 and 20A illustrate another embodiment of a device having a double spreader mechanism design. Two spreader mechanisms, each indicated at 193, are attached by support brackets 192 to the operating room table 162 at opposite sides 168. In one embodiment, the spreader mechanisms 193 may be reversibly attachable to opposite sides 168 of the operating room table 162 at predisposed locking points. In this design, the actuators 118, 120 are connected to arms 108, 102 respectively, and are configured generally as mirror-image L-shaped members. In this design, the actuators 118, 120 have gear teeth, and spreaders 193 may be used as a rack-and-pinion design in order to extend the arms 102, 108 apart. Alternatively, the arm-actuator complexes could be configured as mirror-image T-shaped members.

Figure 21:
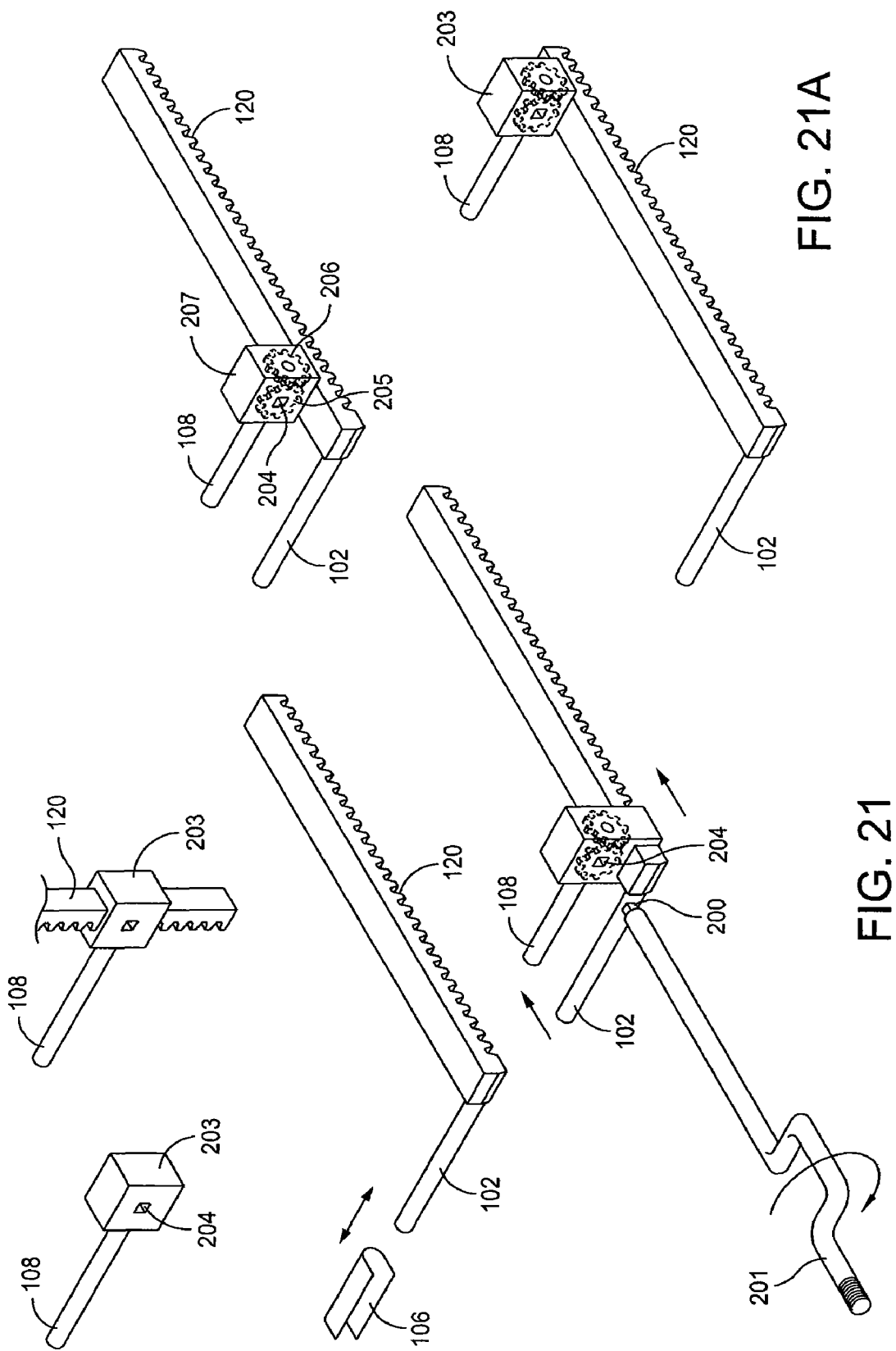

FIGS. 21 and 21A show another embodiment of a device that is meant to be placed completely underneath the skin layer when a tissue plane and space is developed between adjacent muscle and subcutaneous fatty tissue layers. Arm 102 is attached to or reversibly attached to support channel 106 at one end, and to actuator 120 at its other end. Actuator 120 passes through base 203, with the base being attached to arm 108, which in turn is attached to or reversibly attached to support channel 106. Base 203 contains at least one or more gears 205, 206. Gear 205 has a socket 204 into which a crankshaft 201 fits into at its end 200. Crankshaft 201 may be attached to a reversibly attachable to base 203 by adjoining portions 200, 204. When crankshaft 201 is turned, gear or gears 205, 206 interact with the gear teeth of the actuator 120, causing the arms 102 and 108 to extend apart from one another. When crankshaft 201 is turned in the opposite direction, the arms 102, 108 are retracted back to a collapsed position. Typically, with the device completely underneath the skin layer, crankshaft 201 is placed into a separate stab incision 24 (FIG. 33) in order to join end 200 with socket 204 in order to actuate the device and spread the arms 102 and 108 apart underneath the skin layer.

Figure 22:
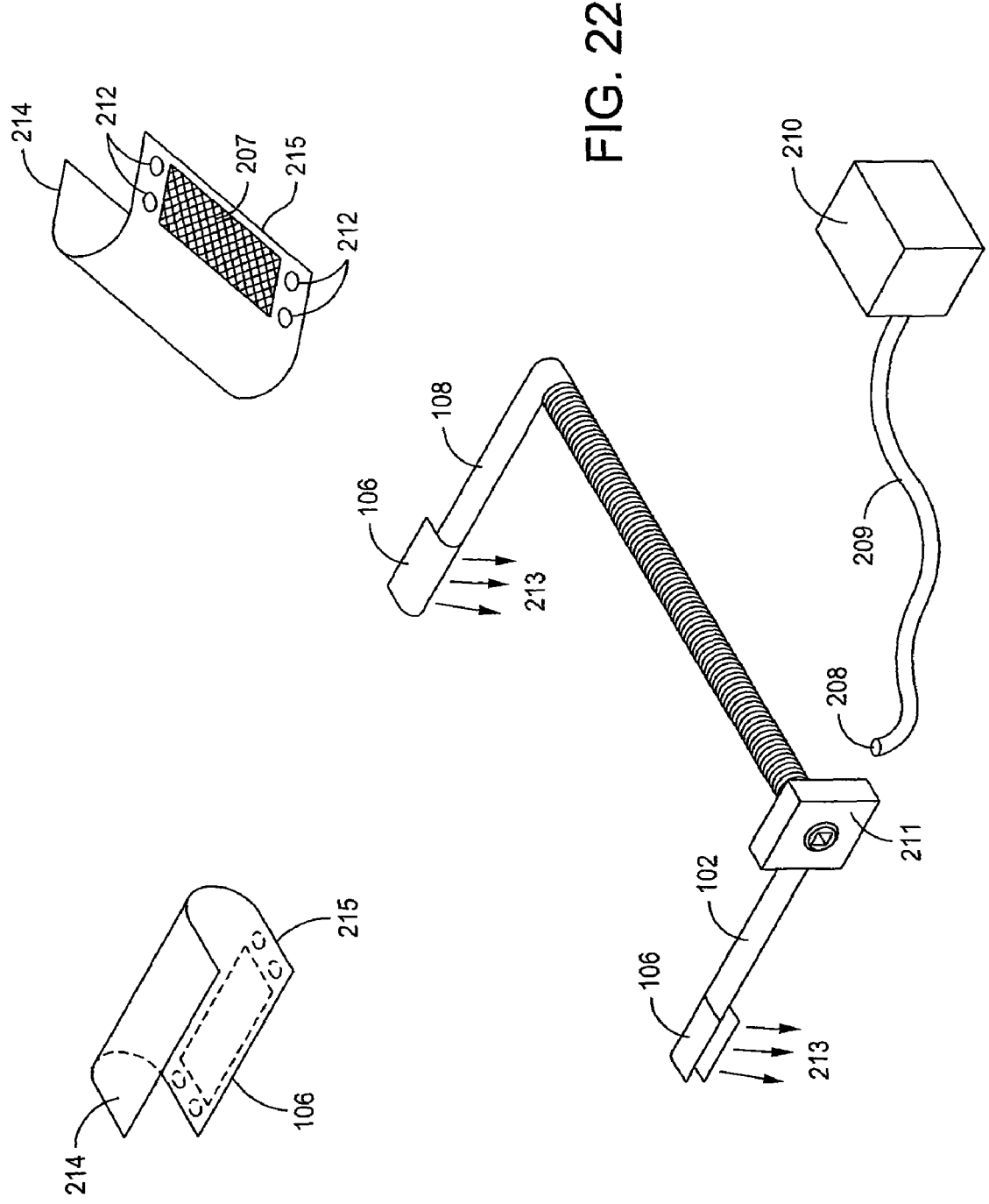
FIG. 22 illustrates an exploded perspective view of a device of the disclosure having arms or support channels that contain an integrated light panel.

FIG. 22 represents another embodiment of a support channel 106 having a light panel 207 that is built into an undersurface of the channel 106. The light source may be fiber-optic, which originates from a generator 210. The light source is delivered through a cable 209 to a connector 208, which is connected to a receptor socket 211. Alternatively, light panels 207 may be powered by batteries 212 integrated into support channels 106. The lighting may be comprised of light emitting diodes (LEDs), or any other suitable light source. The lighting is located on an undersurface 215 of the support channels 106 so that light 213 can be directed below the device when viewed from above. Although shown on undersurface 215, the lighting may be provided on any part of the support channel 106 suitable for illuminating a desired area of a patient.

Figure 23A:
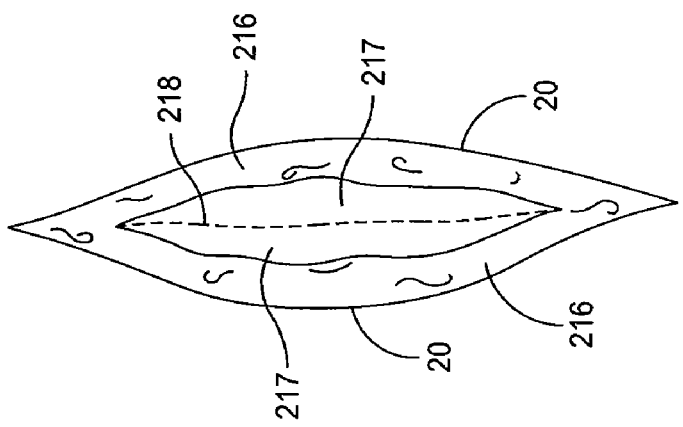
FIGS. 23 and 23A illustrate initial steps of a method of performing surgery through a small skin incision.
Figure 23:
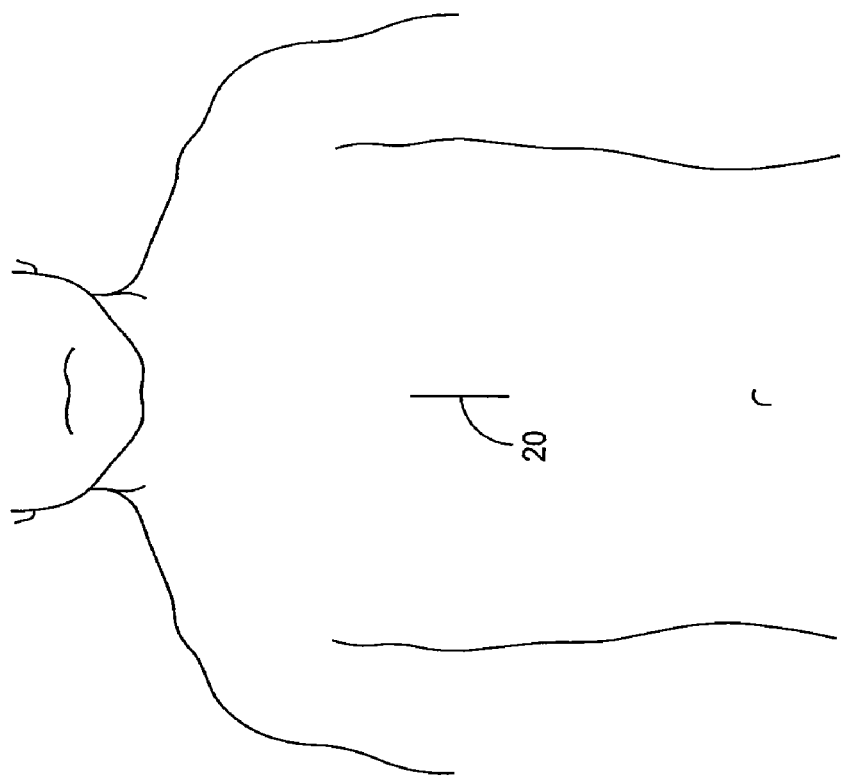

Referring now to FIGS. 23-33, a method of performing surgery is discussed. FIGS. 23 and 23A illustrate the initiation of the method of performing surgery through a small skin access incision 20, which may be 8 cm or smaller. The small access incision 20 shows the layers of soft tissue between the skin 20 and the underlying bony tissue barrier, in this case, the breastbone 218. From external to internal, the access incision layers include skin 20 and fatty tissue 216. Also seen through the small access incision 20 is underlying muscle 217.

Figure 24A:
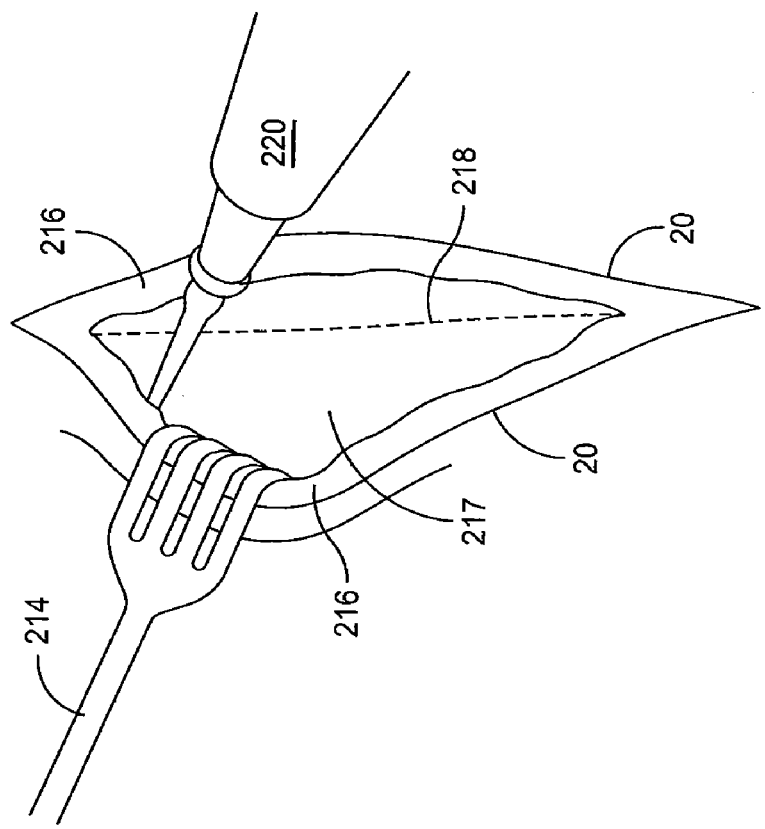
FIGS. 24 and 24A illustrate initiation of a surgical dissection plane between adjacent and overlying muscle and fatty tissue layers.
Figure 24:
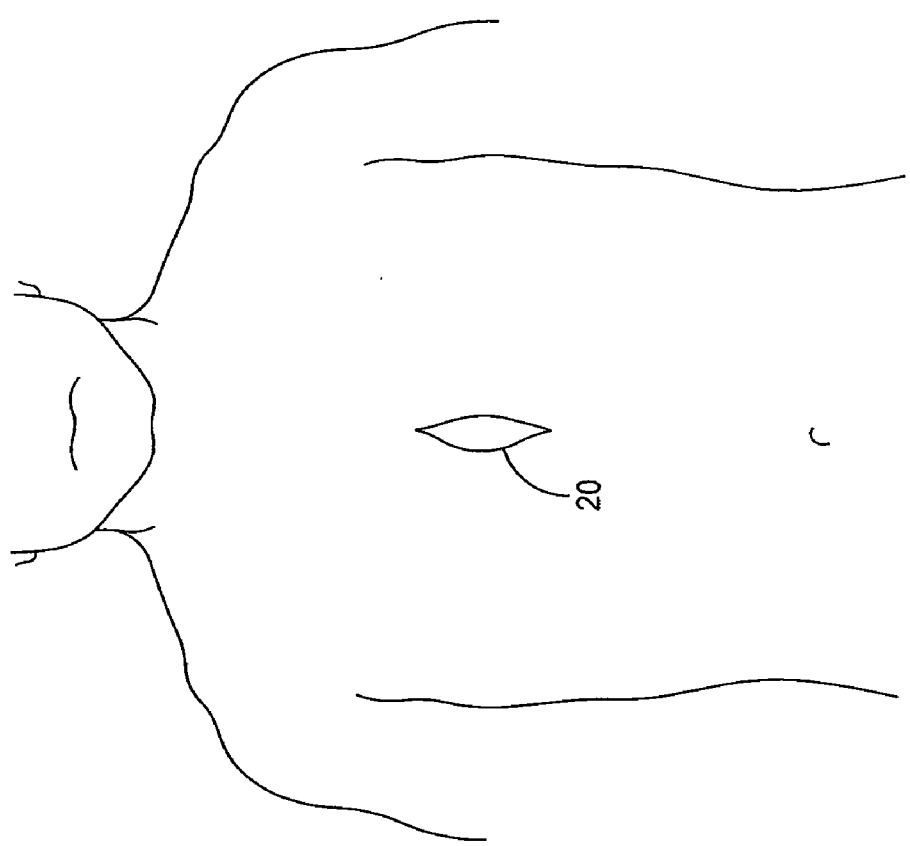

FIGS. 24 and 24A show next steps of the method. A soft tissue rake 219 is used to lift skin 20 and fatty tissue 216 up and away from the muscle layer 217. Both blunt dissection and an electrocautery pen 220 are used to separate the normally adherent fatty tissue and muscle layers.

Figure 25A:
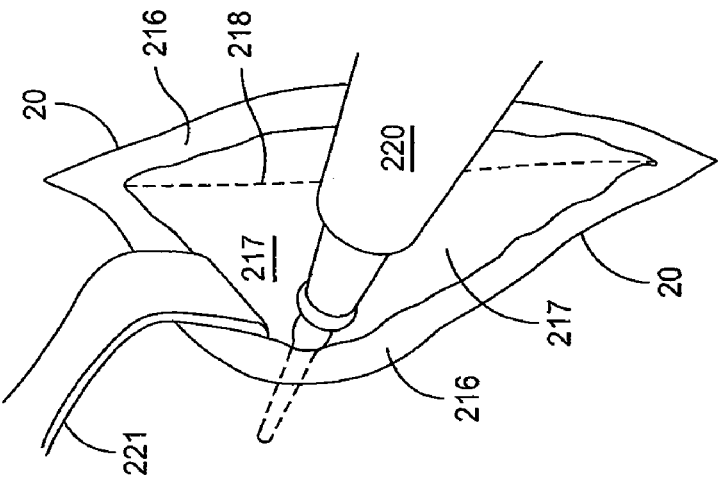
FIGS. 25 and 25A illustrate creation of an extended tissue plane and space between the muscle and fatty tissue layers through a small access incision in the skin and fatty tissue.
Figure 25:
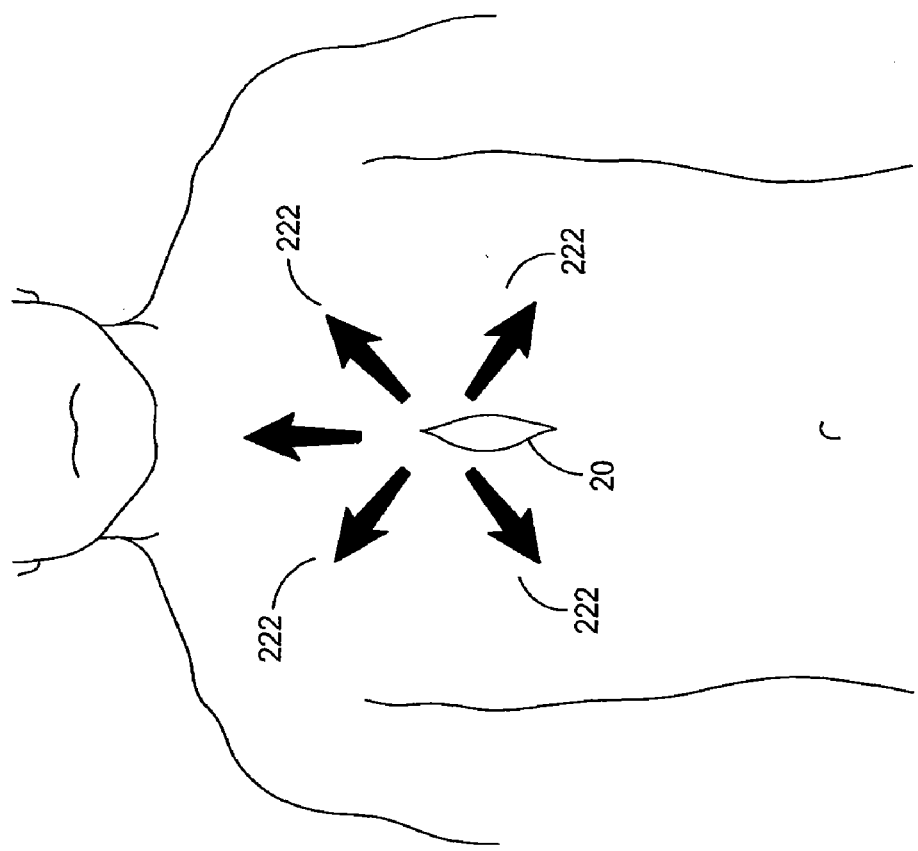

FIGS. 25 and 25A show further progression of the method by extending the dissection between the fatty tissue 216 and the muscle layer 217 to a much larger space 222 radiating in all directions from the small access incision 20. This is accomplished using surgical retractors 221 and an electrocautery 220, as well as blunt surgical dissection.

Figure 26:
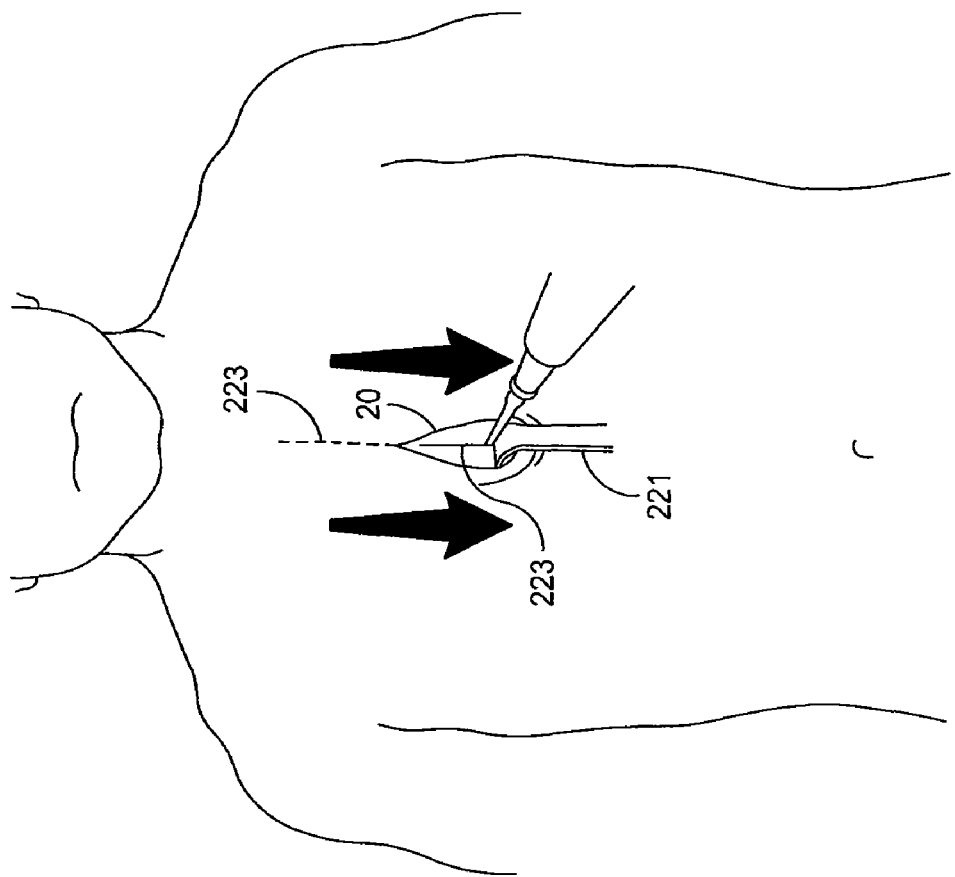
FIGS. 26 and 26A illustrate division of muscle within an extended space created by surgical dissection, thereby exposing the underlying breastbone.
Figure 26A:
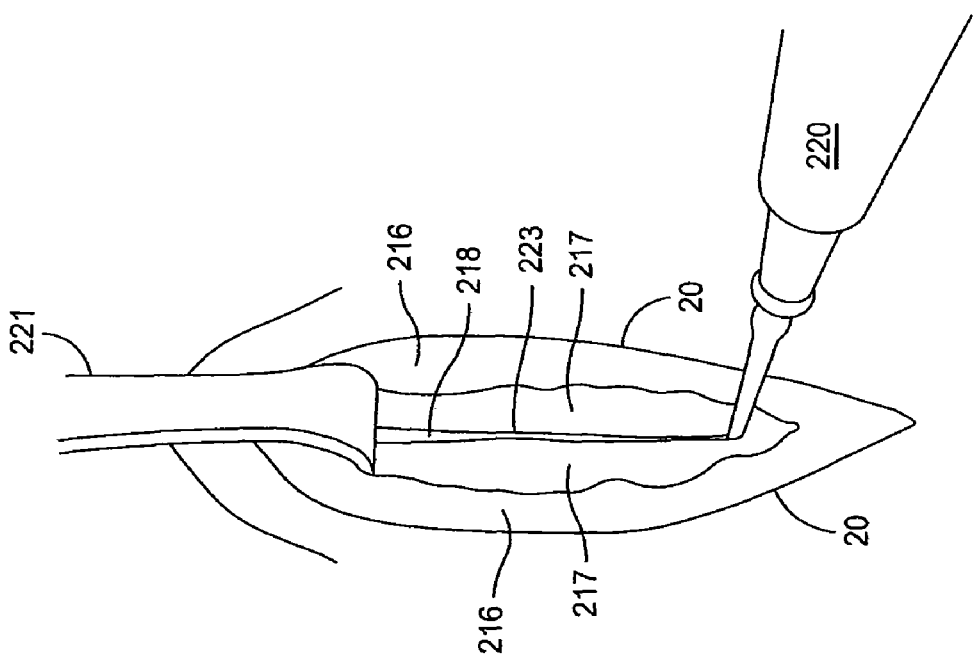

FIGS. 26 and 26A illustrate that after creating the large space under the fatty tissue layer 216, the small access incision 20 becomes quite mobile, and can be manipulated with the surgical retractor 221 in order to gain access to the entire length of breastbone 218 and overlying muscle layer 217. Pectoralis muscle 217 is divided longitudinally along line 223 from its superior to inferior margin, thereby exposing the breastbone underneath.

Figure 27:
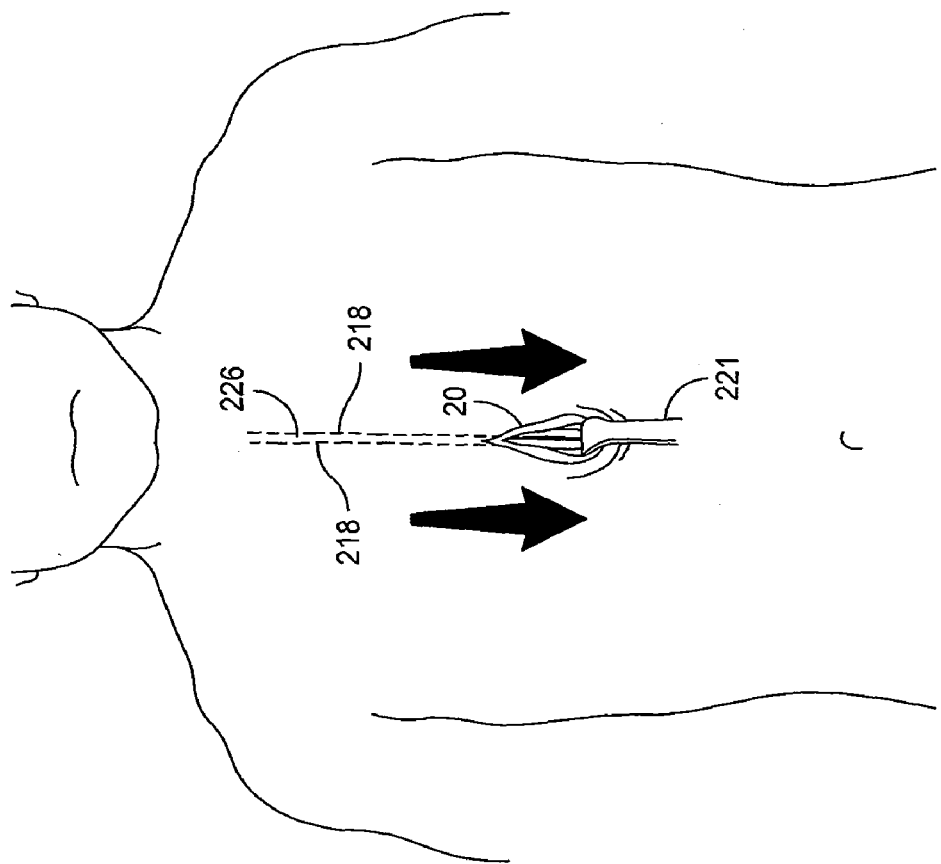
FIGS. 27 and 27A illustrate division of the breastbone with a jigsaw through the small access incision.
Figure 27A:
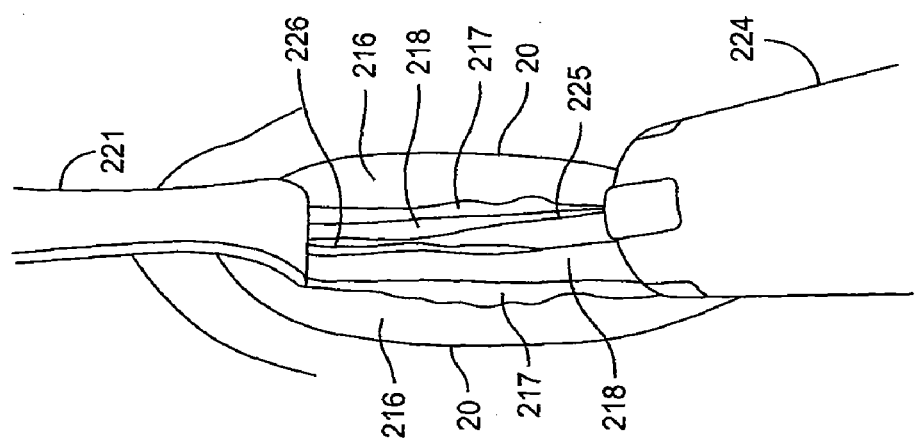

FIGS. 27 and 27A illustrate the use of a standard surgical jigsaw 224 and a blade 225 used to divide longitudinally breastbone 218 through the now mobile access incision 20. The surgical retractor 221 is used to pull traction up or down on access incision 20 in order to expose the upper and lower portions of breastbone 218 to facilitate division.

FIG. 28 shows the completely divided breastbone 218, and the space 226 in between the divided edges, visible through the access incision 20. Also shown are smaller stab incisions 24 that are distinct from access incision 20.

Figure 29:
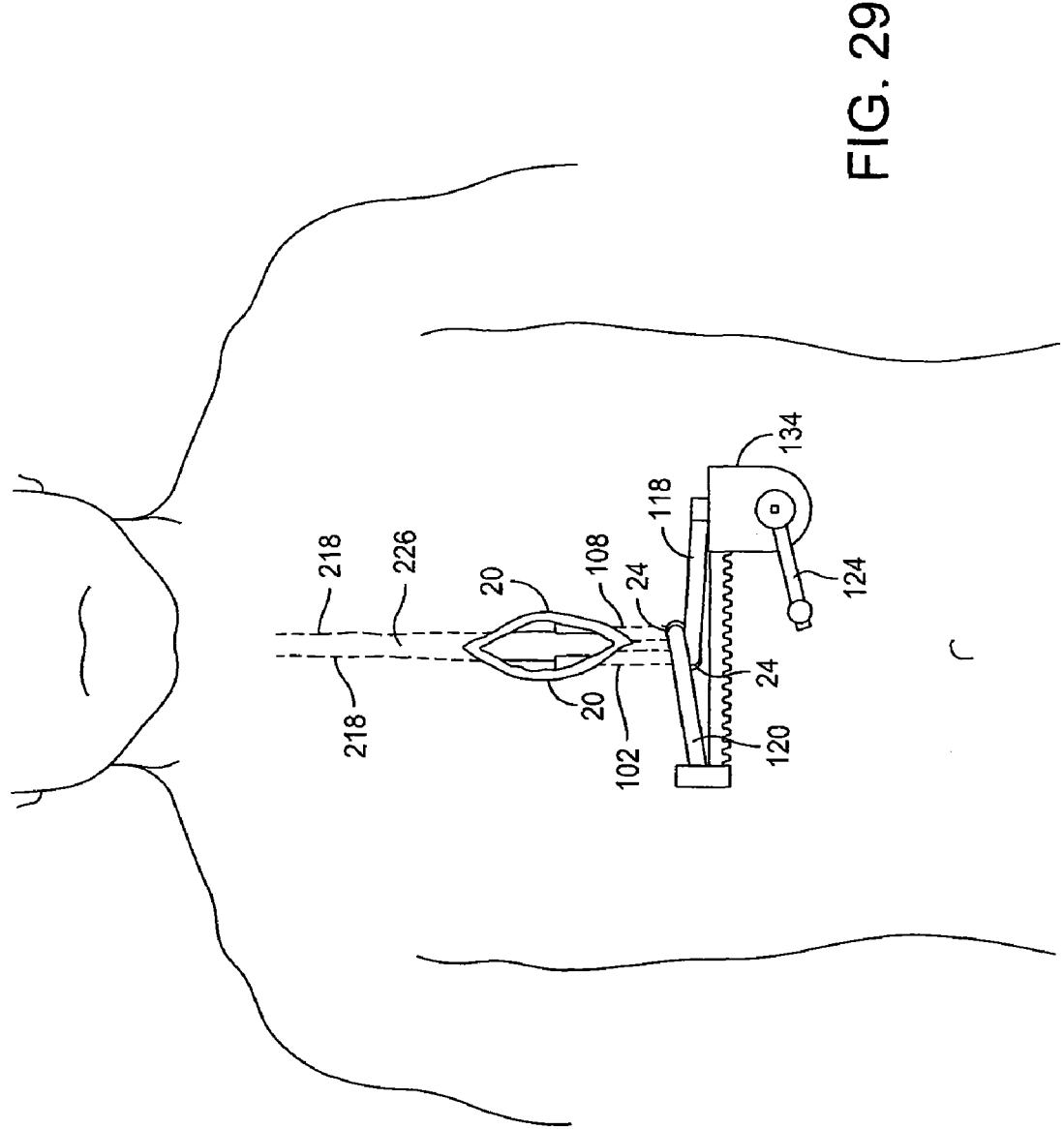
FIG. 29 illustrates insertion of arms of a device through a smaller incision or incisions distinct from the access incision, and advancing them towards the access incision.

FIG. 29 illustrates the insertion of a specialized device created for the method in which the arms 102, 108 are inserted through the distinct stab incisions 24, and advanced towards access incision 20 and into view. At this stage, actuators 118, 120 are external to the skin.

FIGS. 30 and 30A are enlarged views of arms 102, 108 that have been inserted through distinct stab incisions 24. In this iteration, support channels 106 are slid onto arms 102, 108 through the access incision 20. Support channels 106 are applied to the divided edges of breastbone 218 to prepare the device for deployment.

FIGS. 31 and 31A show an iteration of the device in partial stages of deployment. As the hand-crank 124 of the spreader 134 is turned, the actuators 118, 120 are advanced underneath the skin into the created space by access through the distinct stab incisions 24. In the half-deployed position, portions of the actuators 120, 118 are external to the skin, while other portions are underneath, internal to the skin 227, 228, respectively. As the spreader is actuated, the arms 102, 108 and the support channels 106 spread the divided edges of the breastbone 218 apart to create an access space to the deeper tissues 226, which gets larger as the device is expanded.

FIG. 32 illustrates an iteration of the device in a completely extended position. The majority of actuators 118, 120 are now underneath the skin layer, as actuators 227, 228, having been advanced by spreader 134 by access through the distinct stab incisions 24. The attached arms 102, 108 and the support channels 106 extend the divided breastbone edges 218 apart. Because the divided breastbone is spread far apart, the surgeon now can visualize and manipulate typical structures such as the heart, lungs and aorta through access incision 20.

Figure 33:
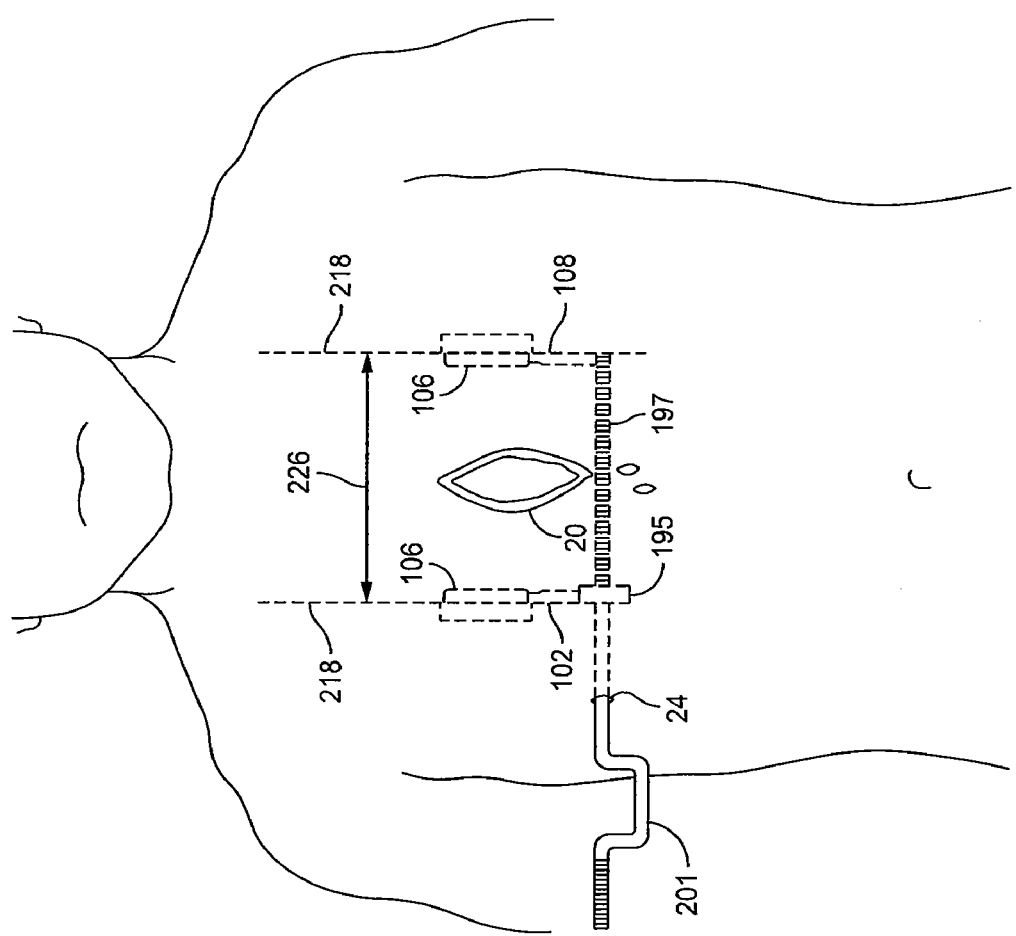
FIG. 33 illustrates the device shown in FIG. 19 in an extended position, with the device fully inserted below the skin and fatty tissue layers after creation of that space, and with a crankshaft being inserted through a separate stab incision distinct from the access incision in order to actuate the device to spread its arms apart.

FIG. 33 is an illustration of a different device, such as the device shown in FIG. 19, in the completely deployed (extended) position. The device is positioned below the skin and fatty tissue layer after creating the space by the method described. The crankshaft 201 is placed through the distinct stab incision 24 in order to join actuator bolt 197, and drive it through base 195. The crankshaft 201 can then be removed from actuator bolt 197 during the procedure. In the extended position, the attached arms 102, 108 and the support channels 106 spread apart the divided breastbone edges 218 in order to maintain deep access space 226, and allow visualization of deep structures through the access incision 20. At the end of the procedure, the crankshaft 201 is turned in the reverse direction to collapse the device to facilitate removal.

FIG. 34 illustrates a device 300 of another embodiment. As shown, the device 300 includes a spreader mechanism 302 having a base 304 and a handle 306. The device further includes an actuator 308 that extends through the base 304 of the spreader mechanism 302. The rotation of the handle 306 of the spreader mechanism 302 causes the relative movement of the actuator 308 with respect to the base 304. As shown, the spreader mechanism 302 further includes another actuator 310, which is fixedly secured to the base 304. Arms 312, 314 are attached to respective actuators 308, 310, with each actuator being curved when transitioning to its respective arm. As shown, actuator 308 overlies arm 314. However, it should be understood that the device 300 may be configured so that arm 314 overlies actuator 308 and fall within the scope of the present disclosure.

In this example, one of the actuators (e.g., actuator 310) is fixed to the base 304 of the spreader mechanism 302, and the other actuator (e.g., actuator 308) is comprised of both a curved segment as well as a straight segment containing gear teeth 316. In another embodiment, both actuators may be configured to have curved and straight segments with gear teeth, and the spreader mechanism is configured to engage each actuator. The spreader mechanism 302 includes gearing or any suitable mechanism provided within the base 304 to actuate the movement of the actuator 308 when turning the handle 306.

Embodiments of the device disclosed herein may be utilized to perform a number of surgical procedures. For example, in a method for performing surgery on organs located below a skin and muscle layer through a small skin incision, the method comprises: making a small access incision in the skin; surgically separating a tissue plane between a normally adherent and adjacently layered muscle and fatty tissue radiating outward from the skin; utilizing a device to spread divided deeper tissues apart below the level of the skin without directly contacting the skin edges of the access incision; and performing a surgical procedure. In one embodiment, the small access incision is generally less than 8 cm long. The device may be configured with a crankshaft driver that traverses from external to, to internal to, the skin in order to actuate and spread the device apart below the intact skin adjacent to the access incision.

In another example, a method for performing heart surgery through a small skin incision comprises: making a small access incision in the skin overlying the breastbone; surgically separating a tissue plane between the normally adherent and adjacently layered pectoralis muscle and fatty tissue radiating outward from the skin incision underneath adjacent areas of intact skin; dividing the pectoralis muscles and the breastbone vertically in the midline; utilizing a device to spread apart the breastbone below the level of the skin without directly contacting the skin edges of the access incision; and performing heart surgery. In one embodiment, the small access incision is generally less than 8 cm long. The device may be configured with a crankshaft driver that traverses from external to, to internal to, the skin in order to actuate and spread the device apart below the intact skin adjacent to the access incision.

In another example, a method for instructing a surgeon to perform heart surgery through a small skin incision comprises: directing the surgeon to create a small access incision in the skin overlying the breastbone; surgically separating the tissue plane between the normally adherent and adjacently layered pectoralis muscle and fatty tissue radiating outward from the skin incision underneath adjacent areas of intact skin; dividing the pectoralis muscles and the breastbone vertically in the midline; utilizing a device to spread apart the breastbone below the level of the skin without directly contacting the skin edges of the access incision; and performing heart surgery. In one embodiment, the surgeon is further instructed to actuate the device by utilizing a crankshaft driver that traverses from external to, to internal to, the skin.

In a further example, a method for instructing a surgeon to perform surgery through a small skin incision comprises: directing the surgeon to create a small access incision in the skin overlying the region of interest; surgically separating the tissue plane between the normally adherent and adjacently layered muscle and fatty tissue radiating outward from the skin incision underneath adjacent areas of intact skin; dividing the muscle layer; and utilizing a device to spread apart the deeper tissues below the level of the skin without directly contacting the skin edges of the access incision, and performing a surgical procedure. In one embodiment, the surgeon is further instructed to actuate the device by utilizing a crankshaft driver that traverses from external to, to internal to, the skin.

Having thus described several aspects of at least one embodiment of this disclosure, it is to be appreciated various alterations, modifications, and improvements will readily occur to those skilled in the art. Such alterations, modifications, and improvements are intended to be part of this disclosure, and are intended to be within the spirit and scope of the disclosure. Accordingly, the foregoing description and drawings are by way of example only.

What is claimed is:

1. A device for expanding an opening formed below a skin layer of a patient, the opening having opposite sides, the device comprising:
   a first arm attached to a first base having a first opening formed therein, the first arm being configured to engage one side of the opening;
   a second arm attached to a second base, the second arm being configured to engage the other side of the opening; and
   a spreader mechanism including a threaded actuator, coupled to the first base of the first arm and the second base of the second arm, to move the first and second arms apart from one another, wherein the first and second arms are configured to move between a retracted position in which the first and second arms are positioned next to one another and an extended position in which the first and second arms are extended to expand the opening,
   wherein the first opening of the first base is threaded to receive the threaded actuator therein so that the first arm moves with respect to the threaded actuator when rotating the threaded actuator, and
   wherein the second base is attached to the threaded actuator so that the second arm remains stationary with respect to the threaded actuator when rotating the threaded actuator.

2. The device of claim 1, wherein each of the first and second arms includes a distracter shaft and a support channel releasably secured to the distracter shaft, the support channel being configured to engage a side of the opening.

3. The device of claim 2, wherein the support channel includes a C-shaped surface adapted to engage body tissue below the skin layer to widen the opening.

4. The device of claim 2, wherein the arms of the device are inserted through at least one site that is separate from a skin incision.

5. The device of claim 2, wherein the device is configured to spread apart the opening without directly spreading apart edges of the skin layer.

6. The device of claim 2, wherein at least one arm or support channel includes an illumination element configured to direct light below the device when viewed from above.

7. The device of claim 1, wherein the spreader mechanism further includes a a device for turning the threaded actuator.

8. A device for expanding an opening formed below a skin layer of a patient, the opening having opposite sides, the device comprising:
   a first arm for engaging one side of the opening;
   a second arm for engaging the other side of the opening;
   a first base member connected to the first arm, the first base member having a first opening formed therein;
   a second base member connected to the second arm; and
   a spreader mechanism including a threaded actuator, coupled to the first base member of the first arm and the second base member of the second arm, to move the arms apart horizontally, wherein the arms are adapted to move between a retracted position in which the arms are positioned next to one another and an extended position in which the arms are extended to expand the opening,
   wherein the first opening of the first base member is threaded to receive the threaded actuator therein so that the first arm moves with respect to the threaded actuator when rotating the threaded actuator, and
   wherein the second base member is attached to the threaded actuator so that the second arm remains stationary with respect to the threaded actuator when rotating the threaded actuator.

9. The device of claim 8, wherein each of the first arm and the second arm comprises a distracter shaft, and a support channel releaseably secured to the distracter shaft, the support channel being configured to engage a side of the opening below the skin layer.

10. The device of claim 9, wherein at least one arm or support channel includes an illumination element configured to direct light below the device when viewed from above.

11. The device of claim 9, wherein the support channel includes a C-shaped surface that is configured to engage a divided breastbone of the patient below the skin layer.

12. The device of claim 8, wherein the arms of the device are inserted through at least one site that is separate from a skin incision.

13. The device of claim 8, wherein the device is configured to spread apart the opening without directly spreading apart edges of the skin layer.

14. The device of claim 8, wherein the spreader mechanism further comprises a a device for turning the threaded actuator.

15. A device for expanding an opening formed below a skin layer of a patient, the opening having opposite sides, the device comprising:
   a first arm for engaging one side of the opening;
   a second arm for engaging the other side of the opening, wherein the first arm is attached to a first base and the second arm is attached to a second base, the first base having a first opening formed therein; and a spreader mechanism including a threaded actuator, actuated by a crank, to move the first and second arms apart, wherein the arms are adapted to move between a retracted position in which the arms are positioned next to one another and an extended position in which the arms are extended to expand the opening, wherein the first opening of the first base is threaded to receive the threaded actuator therein so that the first arm moves with respect to the threaded actuator when rotating the threaded actuator, and wherein the second base is attached to the threaded actuator so that the second arm remains stationary with respect to the threaded actuator when rotating the threaded actuator.

16. The device of claim 15, wherein the device is configured to spread apart the opening without directly spreading apart edges of the skin layer.

17. The device of claim 15, wherein each of the first and second arms includes a distracter shaft and a support channel releasably secured to the distracter shaft, the support channel being configured to engage a side of the opening.

18. The device of claim 15, wherein the threaded actuator is configured as a large bore bolt comprising an external or internal thread and the first opening of the first base through which the threaded actuator passes contains an opposite thread.

* * * * *